(12) United States Patent
Sheldon et al.

(10) Patent No.: US 11,103,186 B2
(45) Date of Patent: Aug. 31, 2021

(54) HEMODYNAMICALLY UNSTABLE VENTRICULAR ARRHYTHMIA DETECTION

(71) Applicant: Medtronic, Inc., Minneapolis, MN (US)

(72) Inventors: Todd J. Sheldon, North Oaks, MN (US); Wade M. Demmer, Coon Rapids, MN (US); Teresa A. Whitman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 78 days.

(21) Appl. No.: 16/511,277

(22) Filed: Jul. 15, 2019

(65) Prior Publication Data

US 2019/0336780 A1     Nov. 7, 2019

Related U.S. Application Data

(60) Continuation of application No. 16/056,676, filed on Aug. 7, 2018, now Pat. No. 10,350,426, which is a
(Continued)

(51) Int. Cl.
*A61B 5/00* (2006.01)
*A61N 1/362* (2006.01)
(Continued)

(52) U.S. Cl.
CPC .......... *A61B 5/686* (2013.01); *A61B 5/6869* (2013.01); *A61N 1/3621* (2013.01);
(Continued)

(58) Field of Classification Search
CPC .............................. A61N 1/3962; A61B 5/686
(Continued)

(56) References Cited

U.S. PATENT DOCUMENTS

| 5,312,454 A | 5/1994 | Roline et al. |
| 5,354,316 A * | 10/1994 | Keimel ............... A61N 1/39622 607/15 |

(Continued)

FOREIGN PATENT DOCUMENTS

| CN | 102015018 A | 4/2011 |
| CN | 102448542 A | 5/2012 |

(Continued)

OTHER PUBLICATIONS

Sheldon, et al., "Hemodynamically Unstable Ventricular Arrhythmia Detection", Chinese Patent Application No. 201580074196.1, Office Action dated Nov. 28, 2019, 7 pages.

(Continued)

*Primary Examiner* — Nadia A Mahmood
(74) *Attorney, Agent, or Firm* — Shumaker & Sieffert, P.A.

(57) ABSTRACT

An implantable medical device system includes a pacemaker and an implantable cardioverter defibrillator (ICD). The pacemaker is configured to confirm a hemodynamically unstable rhythm based on an activity metric determined from an activity sensor signal after detecting a ventricular tachyarrhythmia and withhold anti-tachycardia pacing (ATP) pulses in response to confirming the hemodynamically unstable rhythm. The pacemaker may deliver ATP when a hemodynamically unstable rhythm is not confirmed based on the activity metric. The ICD is configured to detect the ATP and withhold a shock therapy in response to detecting the ATP in some examples.

20 Claims, 8 Drawing Sheets

Related U.S. Application Data division of application No. 14/657,001, filed on Mar. 13, 2015, now Pat. No. 10,052,494.

(60) Provisional application No. 62/095,971, filed on Dec. 23, 2014.

(51) Int. Cl.
*A61N 1/365* (2006.01)
*A61N 1/39* (2006.01)
*A61B 5/363* (2021.01)

(52) U.S. Cl.
CPC ..... *A61N 1/36542* (2013.01); *A61N 1/36578* (2013.01); *A61N 1/36585* (2013.01); *A61N 1/39622* (2017.08); *A61B 5/363* (2021.01)

(58) Field of Classification Search
USPC .......................................................... 607/4
See application file for complete search history.

(56) References Cited

U.S. PATENT DOCUMENTS

| | | | |
|---|---|---|---|
| 5,370,667 A | 12/1994 | Alt | |
| 5,454,838 A | 10/1995 | Vallana et al. | |
| 5,496,361 A | 3/1996 | Moberg et al. | |
| 5,507,782 A | 4/1996 | Kieval et al. | |
| 5,507,785 A | 4/1996 | Deno | |
| 5,545,186 A | 8/1996 | Olson et al. | |
| 5,593,431 A | 1/1997 | Sheldon | |
| 5,628,777 A | 5/1997 | Moberg et al. | |
| 5,683,432 A | 11/1997 | Goedeke et al. | |
| 5,693,075 A | 12/1997 | Plicchi et al. | |
| 5,755,740 A | 5/1998 | Nappholz | |
| 5,836,987 A | 11/1998 | Baumann et al. | |
| 6,393,316 B1 | 5/2002 | Gillberg et al. | |
| 7,031,771 B2 | 4/2006 | Brown et al. | |
| 7,031,772 B2 | 4/2006 | Condie et al. | |
| 7,076,283 B2 | 7/2006 | Cho et al. | |
| 7,130,681 B2 | 10/2006 | Gebhardt et al. | |
| 7,761,142 B2 | 7/2010 | Ghanem et al. | |
| 8,145,307 B2 | 3/2012 | Zhang et al. | |
| 8,160,684 B2 | 4/2012 | Ghanem et al. | |
| 8,315,701 B2 | 11/2012 | Cowan et al. | |
| 8,433,409 B2 | 4/2013 | Johnson et al. | |
| 8,437,842 B2 | 5/2013 | Zhang et al. | |
| 8,457,750 B2 | 6/2013 | Gerber et al. | |
| 8,478,399 B2 | 7/2013 | Degroot et al. | |
| 8,532,785 B1 | 9/2013 | Crutchfield et al. | |
| 8,541,131 B2 | 9/2013 | Lund et al. | |
| 8,744,572 B1 | 6/2014 | Greenhut et al. | |
| 9,724,518 B2 | 8/2017 | Sheldon et al. | |
| 9,814,887 B2 | 11/2017 | Nikolski et al. | |
| 10,226,197 B2 | 3/2019 | Reinke et al. | |
| 2007/0179539 A1 | 8/2007 | Degroot et al. | |
| 2007/0219592 A1 | 9/2007 | Axelrod et al. | |
| 2011/0201945 A1 | 8/2011 | Li et al. | |
| 2012/0101392 A1 | 4/2012 | Bhunia et al. | |
| 2012/0109236 A1 | 5/2012 | Jacobson et al. | |
| 2012/0172892 A1 | 7/2012 | Grubac et al. | |
| 2012/0296387 A1 | 11/2012 | Zhang et al. | |
| 2013/0035748 A1 | 2/2013 | Bonner et al. | |
| 2013/0325081 A1 | 12/2013 | Karst et al. | |
| 2014/0121720 A1 | 5/2014 | Bonner et al. | |
| 2015/0305640 A1 | 10/2015 | Reinke et al. | |
| 2019/0183374 A1 | 6/2019 | Reinke et al. | |

FOREIGN PATENT DOCUMENTS

| | | |
|---|---|---|
| WO | 9527531 A1 | 10/1995 |
| WO | 2007099533 A2 | 9/2007 |
| WO | 2009131768 A1 | 10/2009 |
| WO | 20100138450 A1 | 12/2010 |

OTHER PUBLICATIONS

Raya et al, "Adaptive Noise Canceling of Motion Artifact in Stress ECG Signals Using Accelerometer", Proceedings of the Second Joint EMBS/BMES Conference Houston, TX, USA * Oct. 23-26, 2002, 2 pages.
(PCT/US2015/067343) PCT Notification of Transmittal of the International Search Report and the Written Opinion of the International Searching Authority, dated Mar. 29, 2016, 11 pages.

* cited by examiner

HEMODYNAMICALLY UNSTABLE VENTRICULAR ARRHYTHMIA DETECTION

CROSS-REFERENCE TO RELATED APPLICATIONS

This application is a Continuation of U.S. Ser. No. 16/056,676, (U.S. Publication No. 2018/0339163), filed Aug. 7, 2018, entitled "HEMODYNAMICALLY UNSTABLE VENTRICULAR ARRHYTHMIA DETECTION," which is a Divisional of U.S. Ser. No. 14/657,001, now U.S. Pat. No. 10,052,494, entitled "HEMODYNAMICALLY UNSTABLE VENTRICULAR ARRHYTHMIA DETECTION", filed Mar. 13, 2015, which claims the benefit of U.S. Provisional Application No. 62/095,971, entitled "HEMODYNAMICALLY UNSTABLE VENTRICULAR ARRHYTHMIA DETECTION", filed on Dec. 23, 2014. The content of all of which are incorporated by reference in their entirety.

TECHNICAL FIELD

The disclosure relates to implantable medical device systems including an implantable pacemaker and implantable cardioverter defibrillator and methods for detecting ventricular tachyarrhythmia and controlling tachyarrhythmia therapies delivered by the pacemaker and ICD.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. Other IMDs may incorporate electrodes and/or other sensors along or within a housing of the IMD that encloses circuitry and electronic components of the IMD.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers monitor a patient's heart activity and provide therapeutic electrical stimulation to the heart of the patient via electrodes coupled to the pacemaker. The electrical stimulation provided by the IMD may include signals such as pacing pulses to address abnormal cardiac rhythms such as bradycardia, tachycardia and fibrillation.

An IMD may sense signals representative of intrinsic depolarizations of the heart and analyze the sensed signals to identify normal or abnormal rhythms. Upon detection of an abnormal rhythm, the device may deliver an appropriate electrical stimulation signal or signals to restore or maintain a more normal rhythm. For example, an IMD may deliver bradycardia pacing, anti-tachycardia pacing (ATP), or cardioversion or defibrillation shocks to the heart upon detecting an abnormal rhythm.

In some cases, the IMD senses a signal representative of the metabolic demand of the patient in order to provide cardiac pacing at a rate intended to meet the metabolic demand of the patient. For example, an indication of the patient's physical activity level may be determined from an accelerometer signal in order provide rate responsive pacing to dynamically maintain a heart rate that meets the metabolic demand of the patient.

SUMMARY

In general, the disclosure is directed to techniques for controlling electrical stimulation therapies delivered by an implantable medical device system that includes a cardiac pacemaker capable of delivering anti-tachycardia pacing. A pacemaker operating in accordance with the techniques disclosed herein confirms a hemodynamically unstable rhythm based on an activity sensor signal that comprises heart motion signals. The pacemaker may withhold ATP in response to confirming the unstable rhythm based on the activity sensor signal and deliver ATP in response to not confirming a hemodynamically unstable rhythm based on the activity sensor signal. The system may include an ICD configured to detect ATP delivered by the pacemaker, withhold a shock therapy when ATP delivered by the pacemaker is detected, and deliver a shock therapy when ventricular tachyarrhythmia is detected and ATP is not detected by the ICD.

In one example, the disclosure provides a method performed by an IMD system comprising: sensing a first cardiac electrical signal by an electrical sensing module of a cardiac pacemaker; detecting, by the pacemaker, a ventricular tachyarrhythmia from the first cardiac electrical signal; determining an activity metric from an activity sensor signal received by a control module of the pacemaker; confirming a hemodynamically unstable rhythm based on the activity metric; and withholding anti-tachycardia pacing (ATP) by the pacemaker in response to confirming the hemodynamically unstable rhythm.

In another example, the disclosure provides an implantable medical device (IMD) system comprising an activity sensor and a cardiac pacemaker. The activity sensor is configured to produce a signal correlated to patient activity and comprising heart motion signals. The pacemaker comprises a first sensing module configured to receive a cardiac electrical signal; a pulse generator configured to generate and deliver pacing pulses to a patient's heart via a pair of electrodes; and a control module coupled to the sensing module, the pulse generator and the activity sensor and configured to detect a ventricular tachyarrhythmia from the first cardiac electrical signal, determine an activity metric from an activity sensor signal; confirm a hemodynamically unstable rhythm based on the activity metric, and control the pulse generator to withhold anti-tachycardia pacing (ATP) in response to confirming the hemodynamically unstable rhythm.

In another example, the disclosure provides a non-transitory, computer readable storage medium storing a set of instructions that, when executed by control circuitry of an implantable medical device system, cause the system to sense a first cardiac electrical signal by an electrical sensing module of a cardiac pacemaker; detect, by the pacemaker, a ventricular tachyarrhythmia from the cardiac electrical signal; determine an activity metric from an activity sensor signal received by a control module of the pacemaker; confirm a hemodynamically unstable rhythm based on the activity metric; and withhold anti-tachycardia pacing (ATP) by the pacemaker in response to confirming the hemodynamically unstable rhythm.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
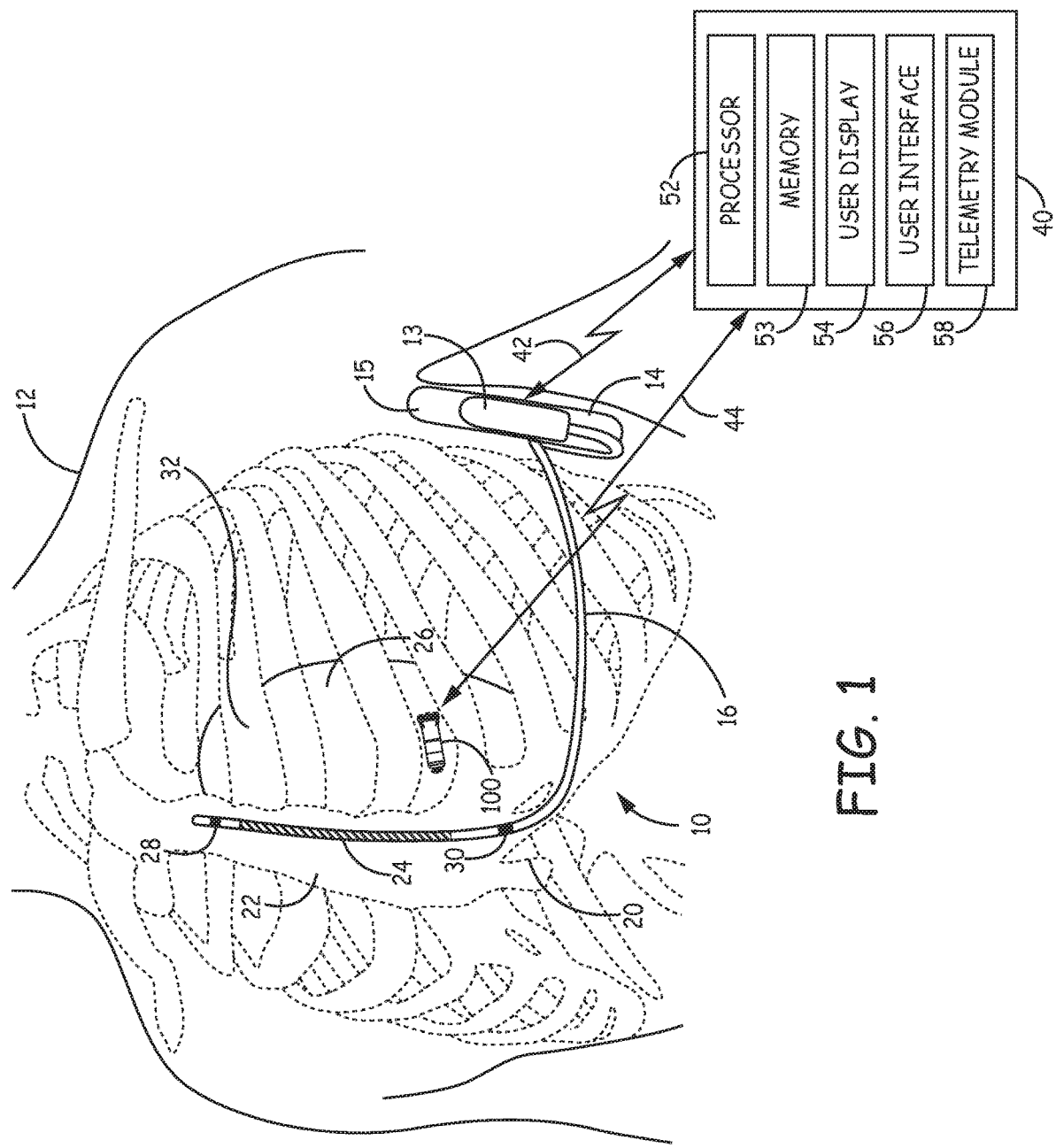
FIG. 1 is a conceptual diagram illustrating an IMD system used to sense cardiac electrical signals in a patient and provide therapies to the patient's heart.

In general, an implantable medical device (IMD) system is disclosed herein that includes a pacemaker configured to deliver cardiac pacing therapies, detect tachyarrhythmia and confirm a hemodynamically unstable tachyarrhythmia based at least in part on an activity sensor signal, e.g., an accelerometer. The pacemaker may be configured to be implanted wholly in a chamber of a patient's heart in some examples. The pacemaker activity sensor is subjected to heart motion so that the activity sensor signal comprises heart motion signals. Therapies delivered by the pacemaker are controlled based at least in part on the activity sensor signal. For example, techniques disclosed herein enable the intracardiac pacemaker to confirm the detection of a hemodynamically unstable rhythm based on the activity sensor signal meeting unstable rhythm detection criteria. The pacemaker withholds ATP in response to confirming the hemodynamically unstable rhythm. The IMD system may further include an ICD configured to detect and treat abnormal rhythms via electrodes coupled to the ICD. The ICD may be configured to detect ATP delivered by the pacemaker and withhold a cardioversion/defibrillation (CV/DF) shock in response to detecting the ATP.

Shockable rhythms refer to abnormal heart rhythms for which a shock therapy is delivered to one or both of the ventricles. Shockable rhythms may include ventricular tachycardia and ventricular fibrillation (VF) and are generally referred to herein as "ventricular tachyarrhythmia" or "VT." Shockable rhythms generally pose an immediate danger to the patient because they are hemodynamically unstable and therapy is needed in order to promote the well-being and safety of the patient. A shock therapy delivered in response to detecting a shockable rhythm generally includes at least one a high-voltage shock pulse, which may be in the range of at least 10 Joules and up to 35 Joules for transvenous lead systems carrying intracardiac cardioversion/defibrillation electrodes and in the range of at least 65 Joules and up to 80 Joules for subcutaneous lead systems carrying extracardiac cardioversion/defibrillation electrodes.

In some instances, VT may be initially treated using an alternative electrical stimulation therapy before attempting a shock therapy, particularly if the VT is hemodynamically stable. The electrical stimulation therapy may be a low-voltage pacing therapy such as anti-tachycardia pacing (ATP), which is relatively painless to the patient compared to a shock therapy. ATP may successfully terminate a VT. If ATP fails, the rhythm may be treated with a shock to terminate the arrhythmia.

Non-shockable rhythms, on the other hand, refer to abnormal or normal heart rhythms that do not require a shock therapy to be delivered to either of the ventricles. Non-shockable cardiac rhythms may include supra-ventricular tachycardia (SVT), which includes sinus tachycardia, atrial tachycardia (AT), atrial fibrillation (AF), atrial flutter, atrio-ventricular nodal reentrant tachycardia (AVNRT), atrioventricular reciprocating tachycardia (AVRT), or the like. Non-shockable rhythms do not generally pose an immediate danger to the patient and may go untreated, i.e., no shock therapy is delivered to the heart.

FIG. 1 is a conceptual diagram illustrating an IMD system 10 used to sense cardiac electrical signals in patient 12 and provide therapy to heart 26. IMD system 10 includes an intracardiac pacemaker 100 and ICD 14 coupled to an extravascular defibrillation lead 16. ICD 14 is implanted subcutaneously on the left side of patient 12. Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is offset laterally to the left side of the body of sternum 22 (i.e., towards the left side of patient 12), offset to the right of sternum 22 or over sternum 22.

Defibrillation lead 16 includes a defibrillation electrode 24, which may be an elongated coil electrode, and a pair of sensing electrodes 28 and 30. Defibrillation lead 16 is placed along sternum 22 such that a therapy vector between defibrillation electrode 24 and the housing 15 of ICD 14 is substantially across one or both ventricles of heart 26. In other examples, another electrode along lead 16 or along a second lead may be used in combination with defibrillation electrode 24 for delivering a shock therapy.

In the example illustrated in FIG. 1, lead 16 is implanted subcutaneously, e.g., between the skin and the ribs or sternum. Lead 16 is advanced suprasternally remaining external to the thoracic cavity. In other embodiments, lead 16 may be advanced substernally or within ribcage 32, i.e., intra-thoracically. For example, lead 16 may be implanted at least partially in a substernal location. In such a configuration, a portion of lead 16 may extend subcutaneously from ICD 14 toward sternum 22 and at least a portion of lead 16 is advanced under or below the sternum in the mediastinum and, more particularly, in the anterior mediastinum. The anterior mediastinum is bounded laterally by pleurae, posteriorly by pericardium, and anteriorly by sternum 22. Lead 16 may be at least partially implanted in other intrathoracic locations, e.g., locations in the region around but not necessarily in direct contact with the outer surface of heart 26. These other intrathoracic locations may include in the mediastinum but offset from sternum 22, in the superior mediastinum, in the middle mediastinum, in the posterior mediastinum, in the sub-xiphoid or inferior xiphoid area, near the apex of the heart, or other location in direct contact or not in direct contact with heart 26 and not subcutaneous.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 may follow a different path, e.g., across the upper chest area and inferior along sternum 22. When the ICD 14 is implanted in the pectoral region, lead 16 or a second lead including a defibrillation electrode may extend along the left side of the patient such that a defibrillation electrode is located along the left side of the patient to function as an anode or cathode of a therapy vector for defibrillating heart 26.

ICD 14 includes a housing 15 that forms a hermetic seal that protects electronic circuitry and other components within ICD 14. The housing 15 of ICD 14 may be formed of a conductive material, such as titanium or other biocompatible conductive material or a combination of conductive and non-conductive materials. In some instances, the housing 15 functions as an electrode (sometimes referred to as a housing electrode or "can" electrode) that is used in combination with one of electrodes 24, 28 and 30 to deliver a therapy to heart 26 or to sense electrical activity of heart 26.

ICD 14 may also include a connector assembly 13 (also referred to as a connector block or header) for receiving a proximal connector (not illustrated) of lead 16. Connector assembly 13 includes electrical feedthroughs through which electrical connections are made between conductors within defibrillation lead 16 and electronic components included within the housing.

Defibrillation lead 16 includes a lead body having a proximal end that includes a connector configured to connect to ICD 14 (via connector assembly 13) and a distal end that includes electrodes 24, 28 and 30. The lead body of defibrillation lead 16 may be formed from a non-conductive material, including silicone, polyurethane, fluoropolymers, mixtures thereof, and other appropriate materials, and shaped to form one or more lumens within which the one or more conductors (not illustrate) each extend to respective ones of electrodes 24, 28 and 30.

When the connector at the proximal end of defibrillation lead 16 is connected to connector assembly 13, the respective conductors electrically couple to circuitry of ICD 14, such as a therapy module and a sensing module via connections in connector assembly 13, including associated feedthroughs. The electrical conductors transmit electrical stimulation pulses from a therapy module within ICD 14 to one or more of electrodes 24, 28 and 30 and transmit sensed electrical signals from one or more of electrodes 24, 28 and 30 to the sensing module within ICD 14. Although defibrillation lead 16 is illustrated as including three electrodes 24, 28 and 30, defibrillation lead 16 may include more or fewer electrodes. For example, two or more sensing electrodes may be included for sensing an ECG signal.

ICD 14 may sense electrical activity of heart 26 via one or more sensing vectors that include combinations of electrodes 28 and 30 and housing 15. For example, ICD 14 may obtain electrical signals, e.g., ECG signals, using a sensing vector between electrodes 28 and 30, between electrode 28 and housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

ICD 14 and pacemaker 100 are each configured to detect ventricular arrhythmias from cardiac electrical signals received via respective electrodes coupled to respective sensing modules within each of the ICD 14 and pacemaker 100. The cardiac electrical signals include cardiac event signals attendant to the depolarization (e.g., R-waves) and the repolarization (e.g., T-waves) of the ventricles.

ICD 14 analyzes sensed ECG signals to detect ventricular tachyarrhythmias (VT), and in response to detecting VT may generate and deliver an electrical therapy to heart 26. For example, ICD 14 may deliver one or more defibrillation shocks via a therapy vector that includes defibrillation electrode 24 and the housing 15. In some instances, IMD system 10 may be configured to deliver one or more pacing therapies prior to or after delivery of a defibrillation shock by ICD 14, such as ATP or post shock pacing.

Pacemaker 100 may be configured to confirm a hemodynamically unstable rhythm based on an activity sensor signal after detecting VT based on a cardiac electrical signal. If the detected VT is confirmed as a hemodynamically unstable rhythm, the pacemaker 100 withholds ATP, allowing ICD 14 to deliver a necessary CV/DF shock. If the detected VT is not confirmed to be a hemodynamically unstable rhythm by pacemaker 100 based on the activity sensor signal, pacemaker 100 delivers ATP. ICD 14 is configured to detect the ATP delivered by pacemaker 100 from an ECG signal received from electrodes 24, 28, 30 and/or housing 15 and withhold a shock until ATP is no longer detected and VT is still being detected.

Alternatively, pacemaker 100 may transmit a wireless telemetry signal to ICD 14 to signal ICD 14 to withhold a shock therapy until an ATP therapy delivered by pacemaker 100 is completed. In other examples, ICD 14 may transmit a communication signal to pacemaker 100 to cause pacemaker 100 to deliver a pacing therapy, such as ATP or post-shock bradycardia pacing, e.g., as generally disclosed in U.S. Pat. No. 8,744,572 (Greenhut, et al.), incorporated herein by reference in its entirety.

In the example shown, pacemaker 100 is a transcatheter, intracardiac pacemaker adapted for implantation wholly within a heart chamber, e.g., wholly within the RV. Pacemaker 100 may be positioned along an endocardial wall of the RV, e.g., near the RV apex, however other locations within or along heart 26 are possible including epicardial locations. Pacemaker 100 is configured to sense an intracardiac electrogram (EGM) signal via one or more electrodes on the outer housing of the pacemaker 100 and produce electrical stimulation pulses, i.e., pacing pulses, delivered to heart 26 via the one or more electrodes on the outer housing of the pacemaker 100.

In other embodiments, pacemaker 100 may be positioned in the left ventricle (LV) of heart 26. In some cases, IMD system 10 may additionally include an intracardiac pacemaker implantable in an atrial chamber for sensing atrial electrical signals and delivering atrial pacing pulses. Techniques disclosed herein are not limited to a pacemaker implantable within a heart chamber. In other examples, pacemaker 100 could be implantable inside or outside heart 26. In each of these examples, pacemaker 100 includes a motion-based patient activity sensor that is subjected to the motion of the beating heart 26 such that an activity sensor signal includes heart motion signals.

Pacemaker 100 and ICD 14 are each capable of bidirectional wireless communication with an external device 40. External device 40 is often referred to as a "programmer" because it is typically used by a physician, technician, nurse, clinician or other qualified user for programming operating parameters in pacemaker 100 and ICD 14. Operating parameters, such as sensing and therapy delivery control parameters, may be programmed into pacemaker 100 and ICD 14 using external device 40. External device 40 may be located in a clinic, hospital or other medical facility. External device 40 may alternatively be embodied as a home monitor or a handheld device that may be used in a medical facility, in the patient's home, or another location. Aspects of external device 40 may generally correspond to the external programming/monitoring unit disclosed in U.S. Pat. No. 5,507,782 (Kieval, et al.), hereby incorporated herein by reference in its entirety.

External device 40 includes a processor 52, memory 53, user display 54, user interface 56 and telemetry module 58. Processor 52 controls external device operations and processes data and signals received from pacemaker 100 and ICD 14. External device 40 may be used to program operating parameters, such as sensing control parameters, tachyarrhythmia detection control parameters, and therapy delivery control parameters used by pacemaker 100 and ICD 14. Processor 52 may provide user display 54 with data for generating a graphical user interface to a user for selecting and programming control parameters.

External device 40 may display other data and information relating to pacemaker 100 and ICD 14 functions to a user for reviewing IMD system operation and programmed parameters as well as EGM and ECG signals or other physiological data that is retrieved from pacemaker 100 and/or ICD 14 during an interrogation session.

In some examples, pacemaker 100 may store activity sensor signal data in conjunction with EGM signal data to be transmitted to external device 40. External device 40 may provide the data to user display 54 for generating a display of activity sensor signal data and cardiac electrical signal data during a detected arrhythmia. The user may evaluate the reliability of the activity sensor signal data, e.g., activity metrics determined from the sensor signal, for use in confirming a hemodynamically unstable rhythm and making ATP therapy delivery decisions by pacemaker 100. The user display 54 may generate a display of activity metric distribution for review by a user.

As described below, the distribution of activity metrics determined over time from the activity sensor signal may be used in establishing an unstable rhythm detection threshold and/or in verifying reliability of the activity sensor signal in confirming a hemodynamically unstable rhythm. In some cases, the user may select and program an unstable rhythm threshold based on a display of the activity metric distribution. The activity metric unstable rhythm threshold is used by the pacemaker 100 in confirming a hemodynamically unstable rhythm and making a decision to deliver ATP or not in response to detecting VT.

User interface 56 may include a mouse, touch screen, keyboard and/or keypad to enable a user to interact with external device 40 to initiate a telemetry session with pacemaker 100 or ICD 14 for retrieving data from and/or transmitting data to pacemaker 100 or ICD 14 for selecting and programming desired sensing and therapy delivery control parameters.

Telemetry module 58 is configured for bidirectional communication with separate implantable telemetry modules included in pacemaker 100 and ICD 14. Telemetry module 58 establishes a wireless radio frequency (RF) communication link 42 or 44 with a targeted one of ICD 14 or pacemaker 100, respectively, using a communication protocol that appropriately addresses the targeted ICD 14 or pacemaker 100. An example RF telemetry communication system that may be implemented in system 10 is generally disclosed in U.S. Pat. No. 5,683,432 (Goedeke, et al.), hereby incorporated herein by reference in its entirety. Telemetry module 58 is configured to operate in conjunction with processor 52 for sending and receiving data via communication link 42 or 44. Communication links 42 and 44 may be established between the respective ICD 14 or pacemaker 100 and external device 40 via a radio frequency (RF) link in the Medical Implant Communication Service (MICS) band, Medical Data Service (MEDS) band, BLUETOOTH® or Wi-Fi.

Telemetry module 58 may be capable of bi-directional communication with ICD 14 or pacemaker 100 over a wide range of distances, e.g., up to approximately 10 meters. In other examples, telemetry communication pacemaker 100 and ICD 14 may require the use of a programming head placed in proximity of the respective pacemaker 100 or ICD 14 to facilitate data transfer. It is contemplated that external device 40 may be in wired or wireless connection to a communications network via telemetry module 58 for transferring data to a remote database or computer to allow remote management of the patient 12.

Figure 2:
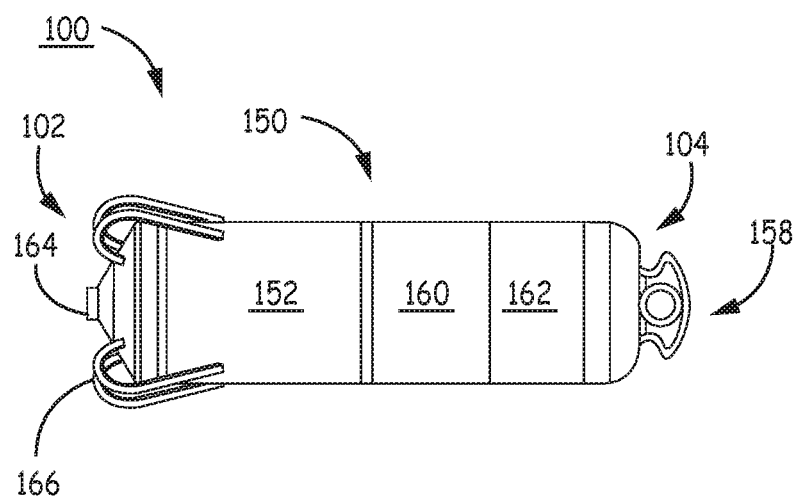
FIG. 2 is a conceptual diagram of intracardiac pacemaker shown in FIG. 1.

FIG. 2 is a conceptual diagram of intracardiac pacemaker 100 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a midportion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form a cathode and anode pair for bipolar cardiac pacing and sensing. Electrodes 162 and 164 may be positioned on or as near as possible to respective proximal and distal ends 104 and 102 to increase the inter-electrode spacing between electrodes 162 and 164. In alternative embodiments, pacemaker 100 may include two or more ring electrodes, two tip electrodes, and/or other types of electrodes exposed along pacemaker housing 150 for delivering electrical stimulation to heart 26 and for sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others.

Electrodes 162 and 164 may be positioned at locations along pacemaker 100 other than the locations shown or along an insulated conductor extending away from housing 150. For example, one or both of electrodes 162 and/or 164 may be carried by a flexible insulated, electrical conductor extending away from housing 150 at proximal end 104 or distal end 102 for increasing the inter-electrode spacing between electrodes 162 and 164. An intracardiac pacemaker having a flexible conductive extender is generally disclosed in commonly-assigned, pre-grant U.S. Publication No. 2013/0035748 (Bonner, et al.), hereby incorporated herein by reference in its entirety.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to or against cardiac tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber. A reduced size of pacemaker 100 enables implantation wholly within a heart chamber. It is recognized that pacemaker 100 may be adapted in size, shape, electrode location or other physical characteristics according to the heart chamber or location in which it will be implanted.

Figure 3:
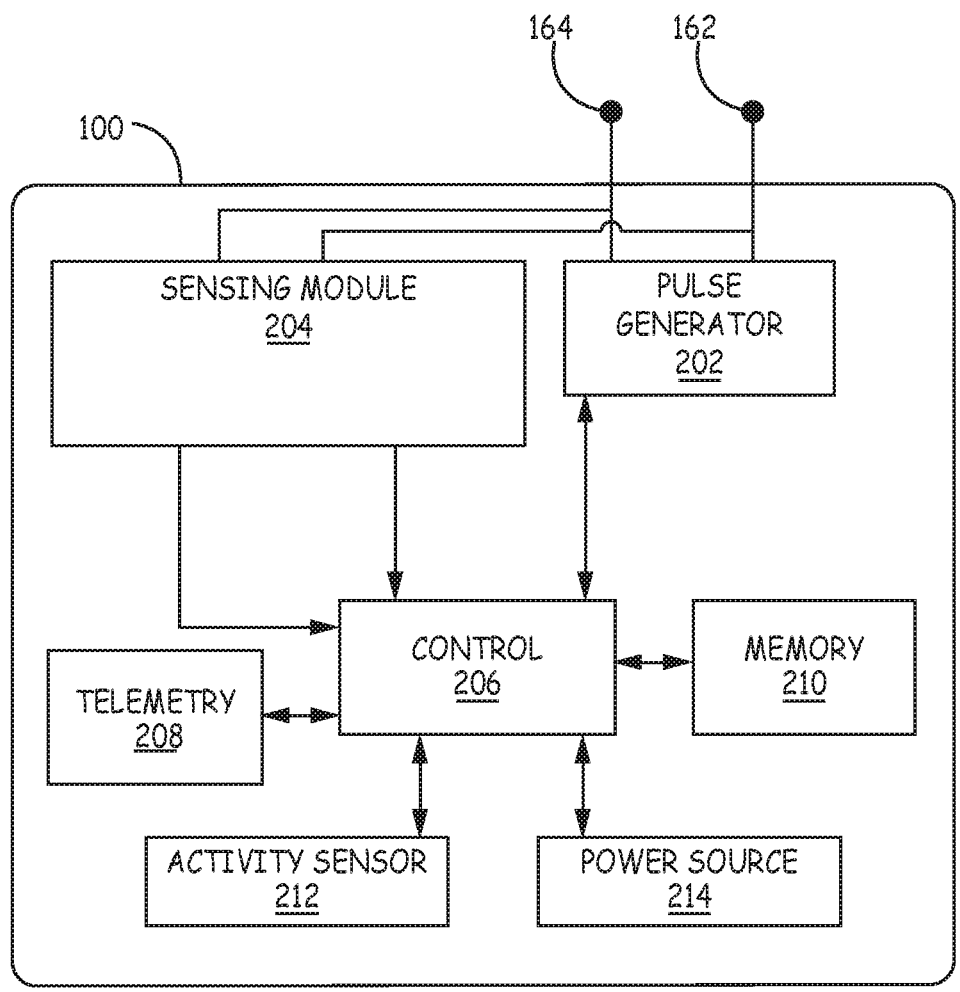
FIG. 3 is a functional block diagram of an example configuration of the pacemaker shown in FIG. 2.

FIG. 3 is a functional block diagram of an example configuration of pacemaker 100 shown in FIG. 2. Pacemaker 100 includes a pulse generator 202, a sensing module 204, a control module 206, telemetry module 208, memory 210, activity sensor 212 and a power source 214. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the IMD system 10 and by the particular detection and therapy delivery methodologies employed by the IMD system 10. Providing software, hardware, and/or firmware to accomplish the described functionality in the context of any modern IMD system, given the disclosure herein, is within the abilities of one of skill in the art. The functions attributed to pacemaker 100 and ICD 14 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate components, or integrated within common hardware, firmware or software components. For example, pacing control operations performed by pacemaker 100 may be implemented in control module 206 executing instructions stored in memory 210 and relying on input from sensing module 204.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202.

Pulse generator 202 generates electrical stimulation pulses that are delivered to heart tissue via electrodes 162 and 164. Electrodes 162 and 164 may be housing-based electrodes as shown in FIG. 2, but one or both electrodes 162 and 164 may alternatively be carried by an insulated, electrical conductor extending away from the pacemaker housing.

Pulse generator 202 may include one or more capacitors and a charging circuit to charge the capacitor(s) to a programmed pacing pulse voltage. At appropriate times, as controlled by a pace timing and control module included in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude and delivering a pacing pulse under the control of control module 206.

Control module 206 controls pulse generator 202 to deliver a pacing pulse in response to expiration of a pacing escape interval according to programmed therapy control parameters stored in memory 210. The pace timing and control module included in control module 206 may include an escape interval timer or counter that is set to a pacing escape interval used for controlling the timing of pacing pulses relative to a paced or sensed event. Upon expiration of a pacing escape interval, a pacing pulse is delivered. If a cardiac event is sensed during the pacing escape interval by sensing module 204, the scheduled pacing pulse may be inhibited, and the pacing escape interval may be reset to a new time interval.

Sensing module 204 receives cardiac EGM signals developed across electrodes 162 and 164. A cardiac event may be sensed by sensing module 204 when the EGM signal crosses a sensing threshold, which may be an auto-adjusting sensing threshold. In response to a sensing threshold crossing, sensing module 204 passes a sensed event signal to control module 206 for use in controlling the timing of pacing pulses.

Pacemaker 100 may be configured to provide rate responsive cardiac pacing to meet the metabolic demand of the patient as the patient transitions between different levels of patient activity, e.g., rest, moderate activity, and maximum exertion. Control module 206 may use a signal from activity sensor 212 for determining a patient-activity based sensor-indicated rate (SIR) used to control the rate of pacing pulse delivery. For example, an escape interval timer included in control module 206 may be set to a pacing escape interval corresponding to a SIR, and the pacing escape interval may be adjusted as the SIR changes in response to the activity sensor signal.

Activity sensor 212 may be embodied as a piezoelectric accelerometer for producing a signal correlated to patient body motion. The use of an accelerometer in an intracardiac device for obtaining a patient activity signal is generally disclosed in U.S. Pat. Publication No. 2015/0217119 filed on Feb. 6, 2014 (Nikolski, et al.), incorporated herein by reference in its entirety. The use of a patient activity signal for providing rate-responsive pacing is generally disclosed in U.S. Pat. No. 7,031,772 (Condie, et al.), incorporated herein by reference in its entirety.

Control module 206 receives an activity signal from activity sensor 212 and may be configured to determine an activity metric from the signal at a desired frequency for use in determining a sensor-indicated pacing rate. The SIR may vary between a programmed lower rate (LR) during periods of rest and a programmed maximum upper pacing rate during periods of maximum exertion. The SIR may be controlled according to a SIR transfer function as described below which may include different rates of change of the SIR over different ranges of the activity metric.

In some examples, the activity metric is determined by control module 206 as an activity count. In these instances, control module 206 includes a counter to track the activity count as the number of times the signal from activity sensor 212 crosses a threshold during an activity count interval, for example a 2-second interval. The count at the end of each activity count interval is correlated to motion imposed on the sensor during the activity count interval, including patient body motion, and can therefore be correlated to patient activity and metabolic demand. In some examples, the activity counts determined over a monitoring interval are used by control module 206 for determining an activity count below which the SIR will remain at the programmed LR. This activity count is referred to herein as the "LR set point." Activity counts below the LR set point indicate a resting state of the patient that does not require pacing above the programmed LR. Control module 206 will determine a SIR that is greater than the programmed LR when the activity count is greater than the LR set point, according to a SIR transfer function.

In other examples, an activity metric may be obtained from the activity sensor signal by integrating or summing activity signal sample points over an activity count interval, e.g., a two second interval though longer or shorter intervals of time may be used for determining an activity metric. In various examples, the activity metrics accumulated over a given time interval are used to determine the LR set point. Methods for establishing and updating a LR set point are generally disclosed in U.S. Patent Publication No. 2016/0144191, filed Nov. 25, 2014 (Demmer, et al.), incorporated herein by reference in its entirety.

As described below, control module 206 is configured to confirm a hemodynamically unstable rhythm based at least in part on a signal from activity sensor 212. The techniques described herein are applicable to an activity sensor that is sensitive heart motion such that an activity metric determined when the patient is still and at rest can have a non-zero value due to heart motion.

A LR set point is an activity metric value that is established by control module 206 to filter baseline heart motion signals from activity metrics that may be used to set a rate responsive pacing rate to meet the metabolic demand of the patient. Activity metrics less than the LR set point but greater than an unstable rhythm threshold represent a normal range of activity metrics obtained when the patient is in a resting state but the activity sensor signal includes heart motion during a hemodynamically stable heart rhythm. The unstable rhythm detection threshold may be defined as an activity metric value that is less than the LR set point. Activity metrics less than the unstable rhythm detection threshold indicate that the heart motion normally contributing to the activity sensor signal has diminished significantly. An activity metric that is less than the unstable rhythm detection threshold indicates a hemodynamically unstable rhythm and therefore a rhythm that warrants immediate shock treatment. In some examples, the unstable rhythm detection threshold may be based on the LR set point that is determined to filter heart motion from activity metrics used for determining a SIR and setting a rate responsive pacing rate.

The pacemaker 100 may be configured to deliver ATP in response to detecting VT if unstable rhythm detection criteria based on the activity sensor signal are not satisfied. If the unstable rhythm detection criteria based on the activity sensor signal are met, the pacemaker 100 does not deliver ATP. ICD 14 detects the shockable rhythm using ECG-based VT detection criteria and delivers an appropriate shock therapy.

Other types of activity sensors other than an accelerometer may produce a signal correlated to the patient metabolic demand. For example, sensors of respiratory activity, such as minute ventilation, blood or tissue oxygen saturation, or another sensor of the patient's body motion or physical activity may be used for providing control module 206 with a signal correlated to metabolic demand for controlling a rate responsive therapy. Various examples of other types of implantable sensors that may be implemented with a rate responsive pacemaker for controlling pacing rate based on metabolic demand are generally described in U.S. Pat. No. 5,755,740 (Nappholz), U.S. Pat. No. 5,507,785 (Deno), and U.S. Pat. No. 5,312,454 (Roline). The techniques disclosed herein may be implemented in conjunction with any type of activity sensor that produces a signal that indicates a non-zero activity level due to heart motion during a resting state, i.e., in the absence of actual physical activity or exertion by the patient.

Pacemaker 100 may further include one or more other physiological sensors for monitoring the patient, such as a pressure sensor, an acoustical sensor, an oxygen sensor, or any other implantable physiological sensor. In some cases, activity sensor 212 may be implemented as a three-dimensional accelerometer used for determining patient activity along any one of the three dimensions and used for detecting changes in patient body posture using the three-dimensional accelerometer signal. A multi-dimensional accelerometer for detecting patient posture changes is generally disclosed in U.S. Pat. No. 5,593,431 (Sheldon), hereby incorporated herein by reference in its entirety.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries.

The connections between power source 214 and other pacemaker modules and components are not shown in FIG. 3 for the sake of clarity.

Telemetry module 208 includes a transceiver and associated antenna for transferring and receiving data from external device 40 via a radio frequency (RF) communication link as described above. Pacemaker 100 may receive pacing and sensing control parameters via telemetry module 208 and store the control parameter values in memory 210 for access by control module 206.

Figure 4:
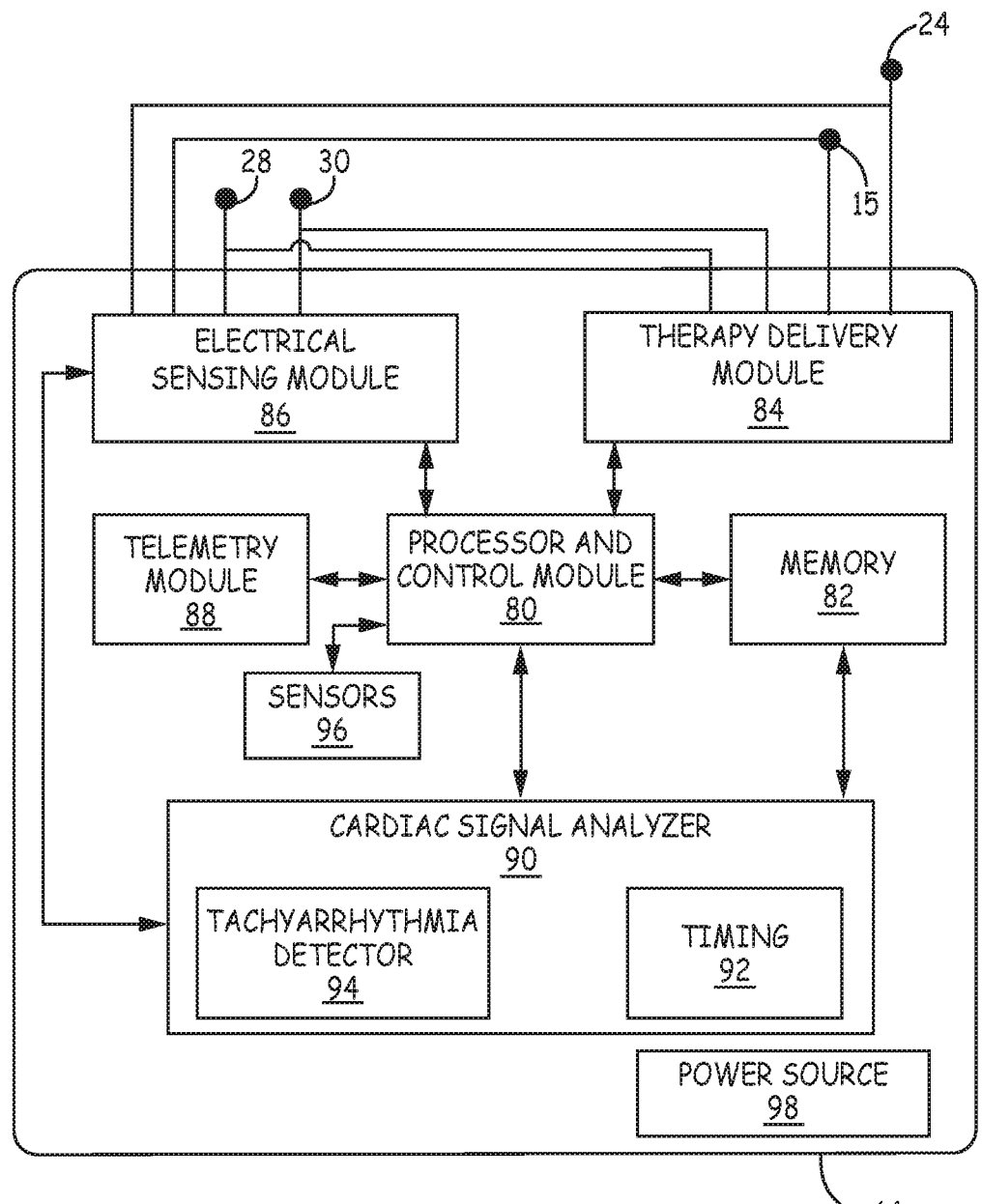
FIG. 4 is a schematic diagram of the ICD shown in FIG. 1 according to one example.

FIG. 4 is a schematic diagram of ICD 14 according to one example. The electronic circuitry enclosed within housing 15 includes software, firmware and hardware that cooperatively monitor one or more ECG signals, determine when a CV/DF shock is necessary, and deliver prescribed CV/DF therapies. In some examples, ICD 14 may be coupled to a lead, such as lead 16, carrying electrodes, such as electrodes 24, 28 and 30, positioned in operative relation to the patient's heart for delivering cardiac pacing pulses, e.g., post-shock bradycardia pacing, in addition to shock therapies.

ICD 14 includes processor and control module 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device.

Furthermore, memory 82 may include non-transitory computer readable media storing instructions that, when executed by one or more processing circuits, cause processor and control module 80 or other ICD modules to perform various functions attributed to ICD 14. The non-transitory computer readable media storing the instructions may include any of the media listed above, with the sole exception being a transitory propagating signal. The functions attributed to IMD system 10 may be executed by system control circuitry including ICD processor and control module 80 and pacemaker control module 206. The system control circuitry may execute instructions stored by discrete or distributed non-transitory, computer-readable storage media to cause IMD system 10 to perform the functions disclosed herein. Processor and control module 80 communicates with therapy delivery module 84, cardiac signal analyzer 90 and electrical sensing module 86 for sensing cardiac electrical activity, detecting cardiac rhythms, and generating electrical stimulation therapies in response to sensed signals. Therapy delivery module 84 and electrical sensing module 86 are electrically coupled to electrodes 24, 28, and 30 carried by lead 16 (shown in FIG. 1) and housing 15, which may serve as a common or ground electrode.

Electrical sensing module 86 is selectively coupled to sensing electrodes 28, 30 and housing 15 in order to monitor electrical activity of the patient's heart. Electrical sensing module 86 may additionally be selectively coupled to defibrillation electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing 15. For example, sensing module 86 may include two sensing channels. Each sensing channel may include a sense amplifier or other cardiac event detection circuitry for sensing cardiac events, e.g., R-waves, from the received ECG signal developed across the selected electrodes 24, 28, 30 or 15. Each time the received ECG signal crosses the auto-adjusting sensing threshold outside a blanking interval, a cardiac event sense signal, such as an R-wave sense event signal, is produced and passed to processor and control module 80 and/or cardiac signal analyzer 90 for use in detecting VT.

Sensing module 86 may include an analog-to-digital converter for providing a digital ECG signal from one or all available sensing channels to processor and control module 80 and/or cardiac signal analyzer 90. For example two ECG signals as described above may each be converted to a multi-bit digital signal by sensing module 86 and provided to tachyarrhythmia detector 94 for performing ECG morphology analysis. Analysis of the ECG signal morphology may be performed by cardiac signal analyzer 90 for detecting VT.

In some examples, sensing module 86 is configured to detect pacing pulses delivered to heart 26 by pacemaker 100. For example, ATP may be delivered by pacemaker 100 in response to pacemaker 100 detecting VT. ICD 14 is configured to withhold or delay a shock therapy when a shockable, VT rhythm is detected by cardiac signal analyzer 90 and ATP pulses are being sensed by sensing module 86. In this way, pacemaker 100 may deliver ATP therapy to terminate the VT precluding the need for a shock. As such, ICD sensing module 86 may include a sensing channel configured with filtering and sensing threshold properties to enable sensing of a pacing pulse to enable ICD 14 to detect ATP pulses being delivered by pacemaker 100. Pacing pulse sensing may correspond to apparatus and techniques generally disclosed in U.S. Patent Publication No. 2015/0305642 and in U.S. Patent Publication No. 2015/0305640, both filed on Apr. 25, 2014 and incorporated herein by reference in their entirety.

ATP may be detected by cardiac signal analyzer 90 when pacing pulse sense event signals are received from sensing module 86 at a rate or interval(s) that meet an expected ATP therapy rate (e.g., versus a bradycardia pacing rate) and/or verifying that the rate of pacing pulse sense event signals are received at a rate that is faster than the immediately preceding detected ventricular rate.

ATP delivered by pacemaker 100 may include a burst of ATP pulses, e.g. 6-16 pacing pulses delivered at intervals that are less than 90% of the detected VT cycle length. Other examples of an ATP therapy delivered by pacemaker 100 may include Ramp ATP that includes a series of progressively faster ATP pulses or Burst+Ramp that includes a fixed rate burst of ATP pulses followed by one or more pulses that are delivered at progressively shorter intervals than the preceding pacing pulse interval. For instance, each successive interval between ATP pacing pulses may be 20 ms shorter than the previous interval during Ramp ATP. Accordingly, ICD 14 may detect ATP when pacing pulses are sensed by sensing module 86 at intervals that are expected during an ATP therapy.

To illustrate, if VT is detected by ICD 14 with a cycle length (RR interval) of 400 ms, ICD 14 may detect ATP delivered by pacemaker 100 in response to sensing a required number of pacing pulses, e.g., at least three pacing pulses, at intervals that are less than 360 ms. A typical ATP therapy delivered by pacemaker 100 in response to detecting VT with the cycle length of 400 ms, and not confirming a hemodynamically unstable rhythm, might be a burst of 8 pacing pulses at 350 ms. As such, ICD 14 will detect the ATP based on sensing pacing pulses at intervals less than 360 ms.

As described below, pacemaker 100 is configured to confirm a hemodynamically unstable rhythm based on the activity sensor signal. If a hemodynamically unstable rhythm is not confirmed, pacemaker 100 delivers ATP, which is detected by ICD 14 causing ICD 14 to withhold or delay a shock. If the VT is redetected after ATP and ATP pulses are no longer detected by ICD 14, processor and control module 80 may control therapy delivery module 84 to deliver the previously withheld or delayed shock.

Cardiac signal analyzer 90 includes a tachyarrhythmia detector 94 for detecting VT and discriminating VT from non-shockable rhythms. Cardiac signal analyzer 90 may further include a timing circuit 92 that includes various timers and/or counters for measuring time intervals, such as RR intervals, setting time windows such as morphology template windows, morphology analysis windows or for performing other timing related functions of cardiac signal analyzer 90 including synchronizing cardioversion shocks or other therapies delivered by therapy delivery module 84 with sensed cardiac events.

In some examples, the timing of R-wave sense event signals received from sensing module 86 is used by timing circuit 94 to determine RR intervals between sense event signals. Tachyarrhythmia detector 94 may count RR intervals measured by timing circuit 92 that fall into different rate detection zones for determining a ventricular rate or performing other rate- or interval-based assessment for detecting VT and discriminating VT and non-shockable rhythms.

Examples of algorithms that may be performed by ICD 14 for detecting, discriminating and treating shockable rhythms, which may be adapted to include techniques described herein for controlling shock therapy delivery, are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening, shockable VT.

Therapy delivery module 84 includes a high voltage (HV) therapy delivery module including one or more HV output capacitors and, in some instances, a low voltage therapy delivery module. When a shockable VT rhythm is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing 15. Timing circuit 92 may be used to control R-wave synchronized shock pulses delivered by therapy delivery module 84.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy.

User-programmable therapy delivery control parameters may be programmed into memory 82 via telemetry module 88. Telemetry module 88 includes a transceiver and antenna for communicating with external device 40 (shown in FIG. 1) using RF communication. Telemetry module 88 may receive downlink telemetry from and send uplink telemetry to external device 40.

ECG episode data related to the detection of VT and the delivery of a cardioversion or defibrillation shock may be stored in memory 82 and transmitted by telemetry module 88 to external device 40 upon receipt of an interrogation command. Clinician review of episode data facilitates diagnosis and prognosis of the patient's cardiac state and therapy management decisions, including selecting programmable control parameters used for detecting shockable VT rhythms and delivering therapy.

In some examples, ICD 14 and pacemaker 100 may be configured to communicate with each other via wireless RF telemetry signals transmitted and received by ICD telemetry module 88 and pacemaker telemetry module 208. In some examples, pacemaker 100 may be configured to transmit an RF signal to ICD 14 to cause ICD 14 to withhold or delay a shock therapy until pacemaker 100 has attempted to terminate a detected tachyarrhythmia by delivering ATP. In other instances, pacemaker 100 may transmit an RF signal to ICD 14 to cause ICD 14 to proceed immediately with a shock therapy without waiting for pacemaker 100 to delivery an ATP therapy.

Figure 5:
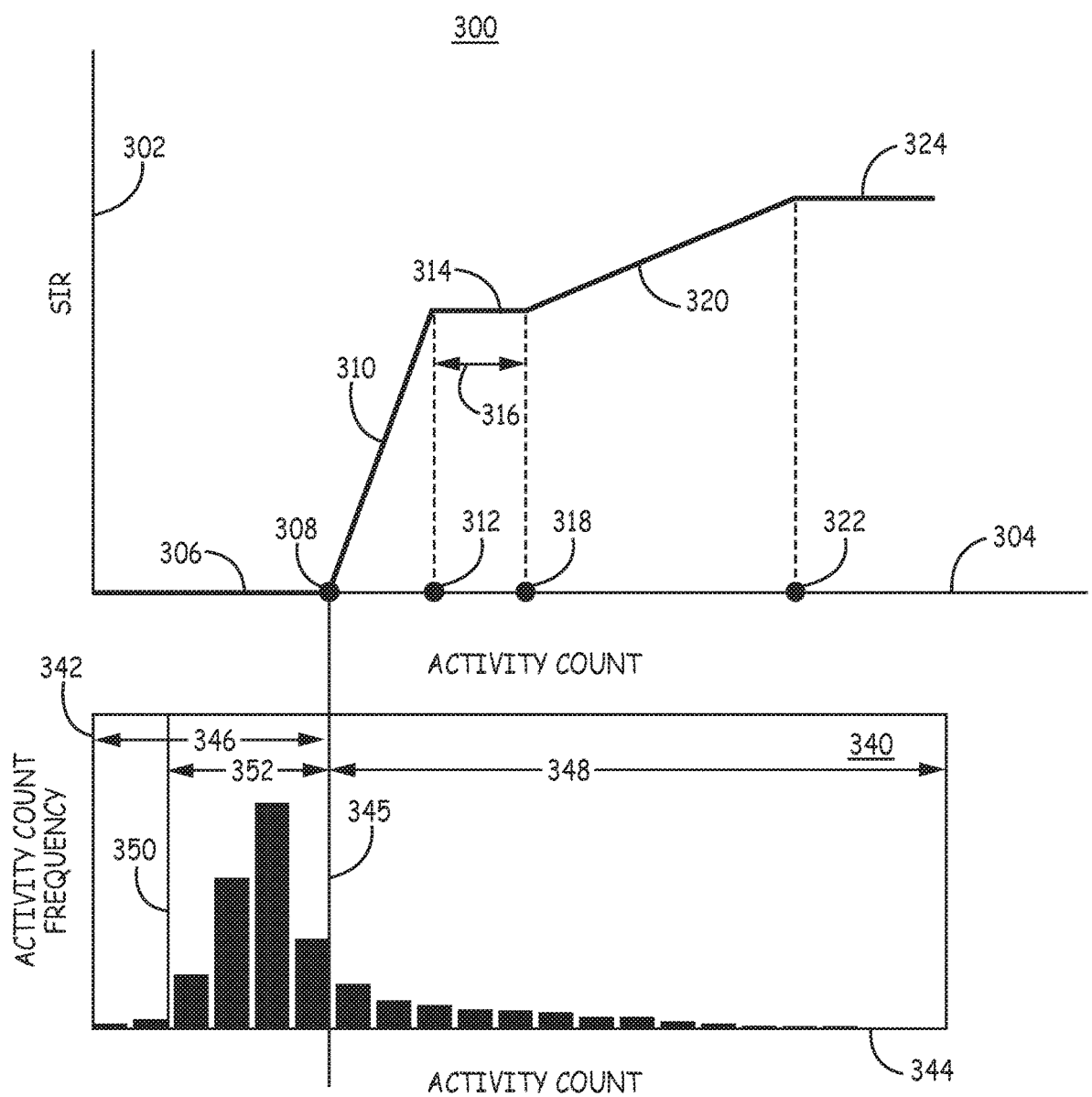
FIG. 5 is a plot of a sensor-indicated rate (SIR) transfer function that may be used by the pacemaker of FIG. 1 for controlling therapies delivered to a patient's heart according to one example.

FIG. 5 is a plot 300 of a sensor-indicated rate (SIR) transfer function that may be used by pacemaker 100 for controlling therapies delivered to heart 26 according to one example. Activity sensor 212 may be an accelerometer that produces a signal correlated to patient body motion. Activity metrics may be determined by pacemaker control module 206 from the accelerometer signal as a count of the total number of threshold crossings of the accelerometer signal or an integrated value of the accelerometer signal over a predetermined n-second interval, e.g., a 2-second interval. The SIR transfer function shown in FIG. 5 may be established using activity counts determined from the accelerometer signal that reflect a patient's activity profile over a typical day or week, user-programmed parameters or a combination of both.

In plot 300, SIR is plotted along the y-axis 302 as a function of activity count plotted along the x-axis 304. Pacemaker control module 206 may establish a lower rate (LR) set point 308 based on an analysis of the activity counts determined over an interval of time. When pacemaker 100 is enabled to provide rate-responsive pacing based on activity counts determined from the activity sensor signal, the pacing rate is not adjusted above a lower rate 306, sometimes referred to as the "base pacing rate," as long as the activity counts are at or below the LR set point 308.

As the activity count increases above the LR set point 308, the SIR may be determined according to the established transfer function between the SIR and the activity count. For example, an activity of daily living (ADL) lower set point 312 and ADL upper set point 318 may be established as the lower and upper boundaries of an activity count range that is expected to encompass the patient's activity level during normal daily activities and moderate activity, such as moving about the house, driving a car, daily chores, etc. The SIR may be increased from the lower pacing rate 306 to the ADL rate 314 according to a slope 310 between the LR set point 308 and the ADL lower set point 312. The SIR remains at the ADL rate 314 over the ADL range 316 between the ADL lower set point 312 and the ADL upper set point 318. An activity count above the upper ADL set point 318 will cause the pacemaker 100 to adjust the SIR according to a second slope 320 as a function of activity count up to a maximum upper rate set point 322. The SIR is set to the maximum upper pacing rate 324 for all activity counts greater than the maximum upper rate set point 322. Each of the lower ADL set point 312, upper ADL set point 318 and maximum upper rate set point 322 may be tailored to a patient's particular needs based on the patient's activity count history.

The LR set point 308 and an unstable rhythm threshold 350 less than the LR set point 308 may be established by the pacemaker 100 based on an analysis of activity counts sampled over an adjustment interval in some examples. For instance, an activity count may be determined every two seconds over a 24-hour adjustment interval. The activity count value at a predetermined percentile 345 of all activity count values accumulated over the adjustment interval is selected as the LR set point 308 in one example. The predetermined percentile 345 may be established as the percentage of time the patient is expected to require pacing at the LR 306, which can also be thought of as the percentage of time that the patient is expected to be at rest or non-active. The activity counts in a resting range 346 extending from an activity count of 0 up to the previously established percentile 345 represent activity counts that may occur when the patient is at rest, e.g., sleeping, napping, sitting or otherwise inactive, and not requiring a pacing rate greater than the lower pacing rate to meet metabolic demand. The activity counts below percentile 345 are highly likely to be due primarily to heart motion and do not represent physical activity of the patient. The activity count values in a non-resting activity range 348 extending from the previously established percentile 345 to a maximum possible activity count represent activity counts that are expected to occur when the patient is active (not resting) and requires a pacing rate greater than the LR 306 to meet the patient's metabolic demand. To illustrate, the percentile 345 may be selected as 85% such that the SIR is at the LR 306 approximately 85% of the time and will be increased above the LR 306 approximately 15% of the time.

The analysis of the activity counts over an adjustment interval may be thought of in terms of a frequency plot 340. The number of activity counts occurring during a predefined time interval is shown along the y-axis 342 for each activity count value shown along the x-axis 344. In one example, the range of possible activity count values may be divided into predetermined activity count bins. The activity counts occurring in each bin are counted over the predefined time interval. The activity count bin at the predetermined patient activity percentile 345 is identified and set as the LR set point 308.

The LR set point 308 may be increased or decreased over time based on accumulated activity counts in order to maintain the number of activity counts that are greater than the LR set point 308 within a range of an expected number of activity counts greater than the LR set point. Continuing with the example given above, if the patient activity percentile 345 is 85%, the activity counts in range 348 greater than the LR set point 308 are expected to be approximately 15% of all the activity counts determined over a given time interval. If more than 15% of the activity counts are greater than the LR set point 308 during a predetermined time interval, the LR set point 308 may be increased. If less than 15% of the activity counts are greater than the LR set point 308, the LR set point 308 may be decreased by pacemaker control module 206. A pacemaker and methods for establishing a LR set point are generally disclosed in the above-incorporated U.S. Patent Publication No. 2016/0144191 filed Nov. 25, 2014.

In addition to establishing LR set point 308, pacemaker control module 206 may establish an unstable rhythm detection threshold 350 for confirming a hemodynamically unstable rhythm based on an analysis of activity counts. The unstable rhythm detection threshold 350 is less than the LR set point 308 and may be defined as a percentile of all activity counts determined over a given time interval, e.g., the first percentile, fifth percentile or tenth percentile of all activity counts. Alternatively, the unstable rhythm detection threshold 350 may be defined as an activity count that is a percentage of the LR set point 308, e.g., 10% or 20% of the LR set point 308. A normal resting range 352 of activity count values occurring between the LR set point 308 and the established unstable rhythm detection threshold 350 represents the range of a vast majority, e.g., 90% or more, of the activity count values that are expected to occur when the patient is in a resting state and the activity count value is due primarily to heart motion. An activity count less than the normal resting range 352 indicates a significant decrease in heart motion that is evidence for confirming a hemodynamically unstable rhythm.

An activity count that is less than the unstable rhythm detection threshold 350, therefore, indicates that even heart motion that normally contributes to the activity sensor signal has diminished significantly. If a fast ventricular rate has been detected by the pacemaker control module 206, the fast rate of the electrical cardiac signals is highly likely to be a hemodynamically unstable rhythm that requires a shock therapy if the activity count is less than the unstable rhythm detection threshold 350, i.e., less than the normal resting range 352 of activity counts.

Figure 6:
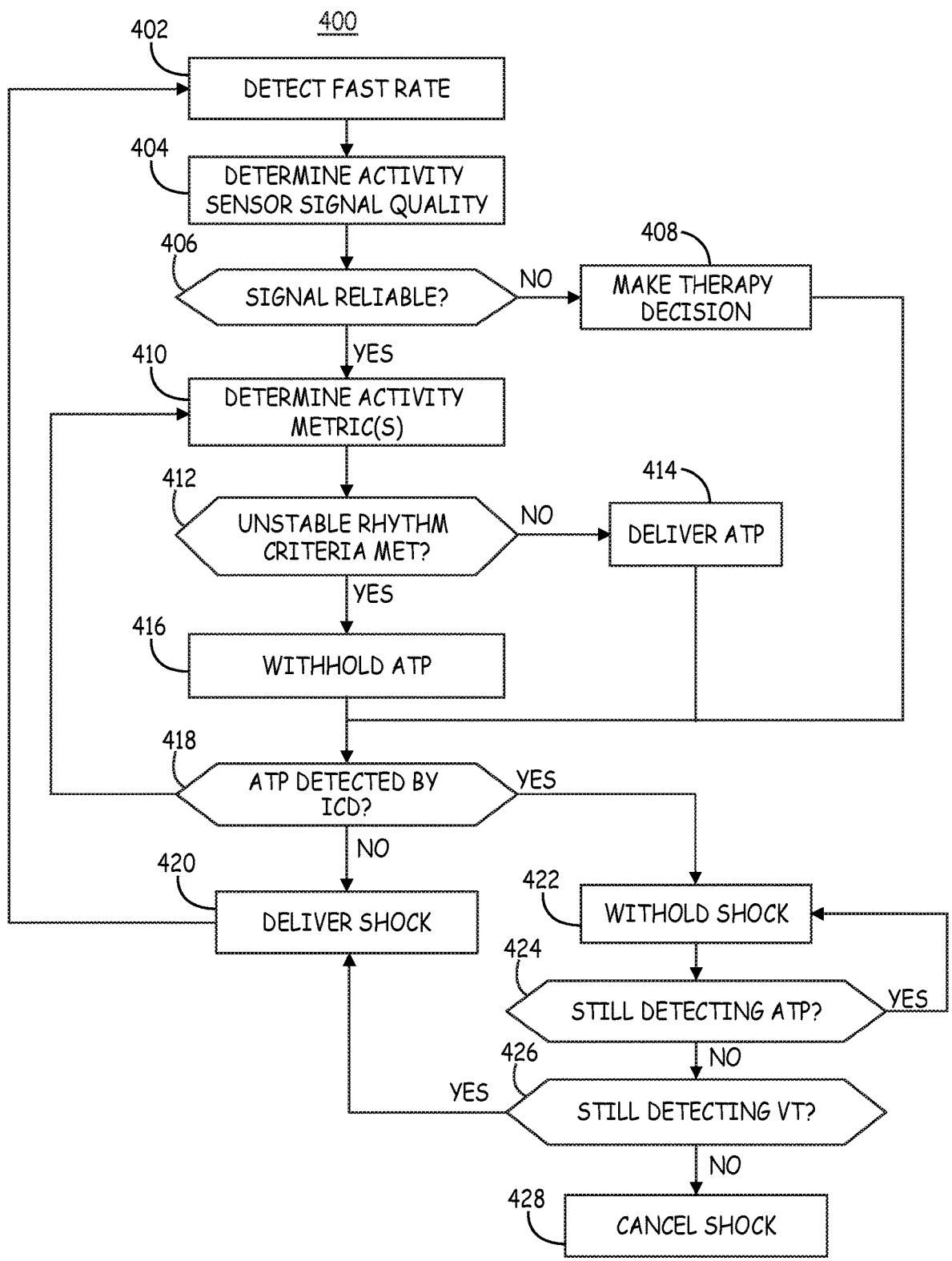
FIG. 6 is a flow chart of a process performed by the IMD system shown in FIG. 1 according to one example.

FIG. 6 is a flow chart 400 of a process performed by IMD system 10 shown in FIG. 1 according to one example. At block 402, the pacemaker 100 detects a fast ventricular rate from the EGM signal received by pacemaker 100. The fast ventricular rate may be detected according to tachyarrhythmia detection criteria of an implemented detection algorithm in pacemaker 100. ICD 14 is expected to simultaneously be detecting a fast ventricular rate from the ECG signal received by ICD 14, based on a tachyarrhythmia detection algorithm implemented in ICD 14. The detection algorithms implemented by pacemaker 100 and ICD 14 may differ. The implemented algorithms may include determining RR intervals between consecutively sensed R-waves and counting RR intervals that fall into VT interval ranges to determine if a required number of VT intervals have been reached to detect VT. Detecting a fast ventricular rate may additionally or alternatively include analyzing R-wave morphology, determining a gross signal morphology, or other analysis of the EGM signal received by the pacemaker 100 or the ECG signal received by ICD 14.

In response to detecting a fast ventricular rate, the pacemaker 100 is configured to confirm that the fast rate is a hemodynamically unstable rhythm based on the activity sensor signal. In some examples, the pacemaker control module 206 may first determine if the activity sensor signal quality is reliable for use in confirming a hemodynamically unstable rhythm to support a therapy delivery decision.

At block 404, pacemaker control module 206 may determine a signal quality metric of the activity sensor signal. In one example, activity counts are determined from the activity sensor signal every two seconds. A signal quality metric may be a determination of the distribution of the activity counts over a preceding time interval to verify that the distribution meets an expected distribution. For example, the pacemaker control module 206 may determine a percentage of activity counts over a preceding time interval (e.g., one or more minutes, one hour, eight hours, or up to 24 hours prior to the onset of the fast ventricular rate) that are greater than the LR set point and/or less than the LR set point. In another example, the pacemaker control module 206 may determine a percentage of the activity counts accumulated over a preceding time interval prior to the onset of the fast ventricular rate that are less than the shock detection threshold.

In yet another example, the pacemaker control module 206 may compare a current distribution of activity counts less than the LR set point 308 to an expected or previous distribution of activity counts less than the LR set point 308. An example distribution of the activity counts less than the LR set point 308 is shown in FIG. 5. If the distribution of activity counts less than the LR set point 308 changes significantly compared to a previous distribution, the activity sensor signal may not be reliable for confirming a hemodynamically unstable rhythm. To detect a significant change in the activity count distribution in the resting range 346, the pacemaker control module 206 may determine a mean, median, mode, standard deviation, total range, lower quartile range, upper quartile range, or any combination thereof and/or other indicator(s) of the distribution of activity counts less than the LR set point 308 and compare the determined indicator(s) to a previous resting range activity count distribution.

Additionally or alternatively, the raw activity sensor signal may be analyzed for signal peaks occurring at regular time intervals as evidence of heart motion during ventricular systole occurring at a regular heart rate prior to the onset of the fast ventricular rate. Regular heart motion signals prior to the onset of the fast ventricular rate would be evidence of a reliable activity sensor signal.

The signal quality metric is compared to reliability criteria at block 406 to determine if the activity sensor signal is reliable for confirming a hemodynamically unstable rhythm. For example, if more than an expected percentage of activity counts are less than the unstable rhythm detection threshold, less than the LR set point, and/or the distribution over the resting range 346 has changed during a preceding time interval prior to the onset of the fast ventricular rate, the activity sensor signal may be deemed unreliable for confirming a hemodynamically unstable rhythm. Additionally or alternative, the percentage of activity counts greater than the LR set point may be compared to an expected target percentage at block 406 for determining if the activity sensor signal is reliable. If the percentage of activity counts greater than the LR set point fall outside the expected percentage range, the activity sensor signal may be determined to be unreliable.

Various activity sensor signal quality metrics may be determined and compared to signal reliability criteria for determining if the activity sensor signal is reliable for use in discriminating between a hemodynamically unstable and hemodynamically stable rhythm. Generally, the determination made at block 410 is whether the activity metrics accumulated over a preceding time period are within an expected distribution or represent an unexpected distribution of activity metrics when a tachyarrhythmia is not being detected, e.g., during a normal sinus or paced rhythm. An unexpected distribution indicates that the activity sensor may be functioning unreliably or the sensor signal has become corrupted.

If the activity sensor signal is deemed unreliable based on an unexpected distribution of activity counts over a preceding time interval or other reliability criteria, a therapy decision is made at block 408 by the pacemaker control module 206 without the use of the activity sensor signal. The decision to deliver ATP or not is based on the EGM signal analysis only (or in combination with signals from other sensors that may be available other than the activity sensor 212). In some examples, if the activity sensor signal is considered unreliable for confirming a hemodynamically unstable rhythm, pacemaker 100 withholds therapy, and therapy delivery is controlled by ICD 14. At block 418, ICD 418 will not detect ATP delivery by pacemaker 100 and will proceed with shock delivery at block 420 if the ICD 14 is detecting VT based on the VT detection algorithm implemented in ICD 14.

If the activity sensor signal is determined to be reliable at block 406, the pacemaker control module 206 determines the activity metric from the activity sensor signal at block 410 in response to detecting the fast ventricular rate. The activity metric may be determined at the expiration of each one or more time intervals after the fast rate is detected. Additionally or alternatively, one or more activity metric values determined immediately prior to the criteria being met for detecting a fast ventricular rate may be used for confirming the fast rhythm is a hemodynamically unstable rhythm.

The one or more activity metrics are analyzed at block 412 to determine if unstable rhythm criteria are met. For example, at least one activity metric is compared to an unstable rhythm detection threshold at block 412. An activity metric less than the unstable rhythm detection threshold, e.g., less than a normal resting activity metric range 352, is evidence of a hemodynamically unstable rhythm. One or more activity metrics less than the unstable rhythm detection threshold may be required to confirm a hemodynamically unstable rhythm. Examples of methods for determining if unstable rhythm criteria are met at block 412 are described below in conjunction with FIGS. 7 and 8. If the unstable rhythm criteria are not met, the fast ventricular rate is detected as a hemodynamically stable VT, and ATP may be delivered at block 414. Before delivering ATP, pacemaker control module 206 may be configured to verify that a shock, delivered by the ICD 14, has not been sensed by the pacemaker sensing module 204 after the fast ventricular rate was detected or during a predefined preceding time interval.

In one example, at least two activity metrics are determined at block 410 as activity counts determined at two consecutive 2-second intervals. The two activity counts may be the most recent two activity counts determined after the onset of the fast ventricular rate but prior to VT detection criteria being met. In other cases, one activity count after the onset of the fast ventricular rate and prior to EGM-based VT detection criteria being met and one activity count after VT detection are compared to the unstable rhythm criteria. In one example, if at least one of the two activity counts is less than the unstable rhythm threshold 350 (FIG. 5), the rhythm is confirmed to be a hemodynamically unstable rhythm. In another example, both of the two consecutive activity counts must be less than the unstable rhythm threshold 350 in order to confirm a hemodynamically unstable rhythm. In other examples, more than two activity counts are used for confirming the hemodynamically unstable rhythm.

If a hemodynamically unstable rhythm is confirmed, ATP is withheld by the pacemaker 100. The ICD 14 does not detect ATP at block 418 and delivers a CV/DF shock at block 420 as long as other shockable rhythm detection criteria used by the ICD 14 have been met.

If the activity metrics determined at block 410 do not meet unstable rhythm criteria at block 412, the pacemaker control module 206 controls pulse generator 202 to deliver ATP at block 414. In one example, ICD cardiac signal analyzer 90 and/or processor and control module 80 is/are configured to detect the ATP pulses at block 418 based on a rate or expected pattern of pacing pulse sense event signals received from ICD sensing module 86. In response to detecting ATP pulses, the ICD processor and control module 80 controls the therapy delivery module 84 to withhold shock therapy at block 422 until ATP pulses are no longer detected (block 424) and a shockable, VT rhythm is still being detected (block 426). If ATP pulses are no longer detected, and a shockable, VT rhythm is still being detected by ICD 14, the shock is delivered at block 420. If ATP pulses are no longer detected and VT is no longer detected, (ATP was successful in terminating the VT), a scheduled shock is cancelled at block 428.

In some cases, more than one ATP attempt to terminate the detected VT may be made by pacemaker 100 at block 414. Accordingly, the ICD 14 may detect more than one ATP sequence at blocks 418 and 424 and delay a scheduled shock until ATP is no longer detected. In other examples, the pacemaker 100 may be configured to deliver a single ATP sequence, and ICD cardiac signal analyzer 90 may be configured to re-detect the shockable, VT rhythm and deliver a delayed shock at block 420 after a predetermined shock delay interval after ATP detection if the shockable rhythm is still being detected (block 424). ICD 14 may be configured to wait for a maximum time interval for delivering a delayed shock. The maximum time interval may correspond to a maximum number of attempts of ATP.

Figure 7:
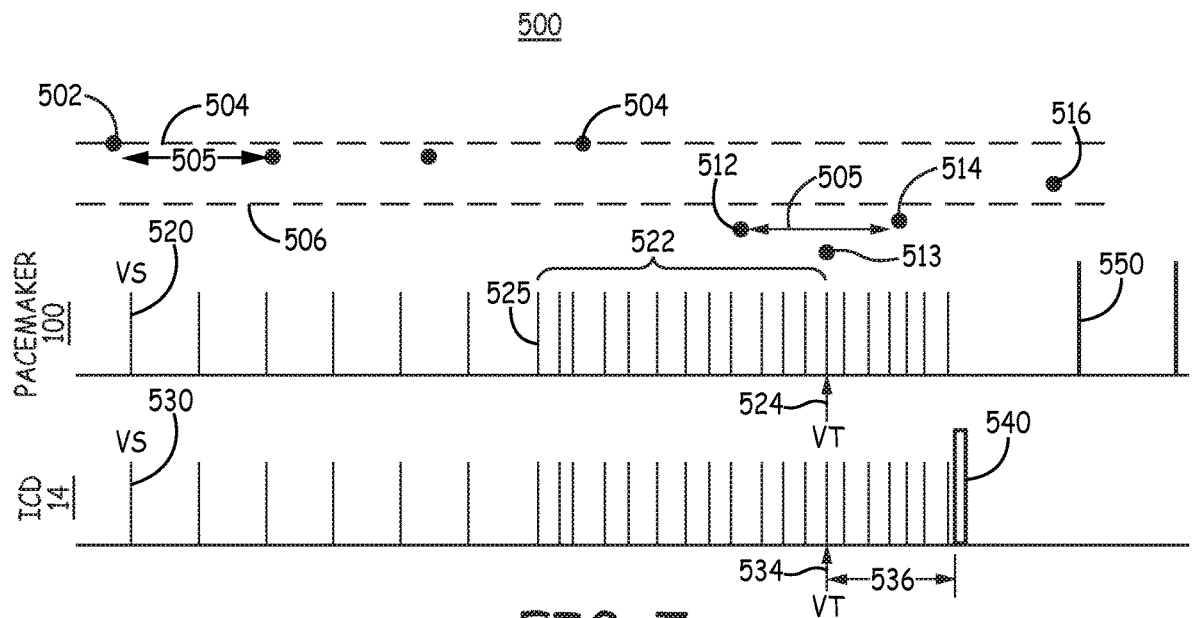
FIG. 7 is a timing diagram illustrating the operations of IMD system of FIG. 1 according to one example.

FIG. 7 is a timing diagram 500 illustrating the operations of ICD 14 and pacemaker 100 according to one example. Pacemaker control module 206 determines activity counts 502, 510, 512, 514, 516 (or another activity metric) at regular activity count sampling intervals 505, e.g., every 2 seconds. A LR set point 504 and an unstable rhythm detection threshold 506 are shown by dashed lines. The LR set point 504 and the unstable rhythm detection threshold 506 may be established by pacemaker 100 based on an analysis of activity counts accumulated over a monitoring time period as described above. Rate-responsive pacing may or may not be enabled in pacemaker 100. The LR set point 504 and unstable rhythm detection threshold 506 are determined as the range of activity counts expected to occur as a result of normal heart motion, when the patient is not exercising. Activity counts less than the unstable rhythm detection threshold 506 are indicative of a hemodynamically unstable rhythm. If rate responsive pacing is enabled, activity counts at or less than the LR set point 504 are used to set the pacing rate to the programmed lower rate and activity counts greater than the LR set point 504 are used to increase the pacing rate to a rate faster than the programmed lower rate according to a SIR transfer function, e.g., the transfer function shown in FIG. 5.

Activity counts in the range between LR set point 504 and unstable rhythm threshold 506 represent counts due to heart motion, and activity counts less than the unstable rhythm threshold 506 represent counts expected when heart motion is significantly altered or diminished due to a hemodynamically unstable tachyarrhythmia. Unstable rhythm detection threshold 506 is less than the LR set point 504, at which the patient is considered to be at rest or non-active, and may be set based on LR set point 504. As such, the unstable rhythm detection threshold 506 is not merely an indication of a patient's resting condition or inactive state since the patient's normal resting condition activity count range exists primarily between LR set point 504 and unstable rhythm detection threshold 506. Unstable rhythm detection threshold 506 represents a decrease from an activity count during normal heart motion at rest to an activity count less than the normal resting range 352 (FIG. 5), indicative of a significant decrease in overall heart motion due to a hemodynamically unstable rhythm.

Pacemaker 100 senses ventricular events 520 and is configured to detect VT based on an analysis of the EGM signal(s) received by sensing module 204. In the example of FIG. 7, a series of ventricular sensed events 522 meet RR interval-based VT detection criteria resulting in VT detection 524. In some cases, if at least eight out of twelve RR intervals are less than a VT detection interval, e.g., less than 300 ms, VT is detected. In other examples, up to 24 RR intervals or more may be required for making a VT detection, e.g., 16 out 24 RR intervals may be required to be VT intervals, depending on the on the particular VT detection criteria implemented in pacemaker 100 and programmed detection parameters.

Upon detecting VT 524, pacemaker 100 analyzes one or more activity counts to confirm a hemodynamically unstable rhythm. In one example, at least the most recent activity count 512 preceding VT detection 524 is compared to the unstable rhythm detection threshold 506. In another example, at least the first or earliest activity count 514 immediately after VT detection 524 is compared to the unstable rhythm detection threshold 506. One or more activity counts 510, 512 preceding the VT detection 524 after the onset of the fast VS events 522 and/or one or more activity counts 514 after the VT detection 524 may be used in confirming a hemodynamically unstable rhythm.

The number of activity counts or other activity metrics used to confirm a hemodynamically unstable rhythm in response to EGM-based VT detection 524 may depend at least in part on the sampling interval 505 between activity counts and the time required to make the EGM-based VT detection 524 after onset of the fast rate of VS events 522. In the illustrative example given above, activity counts 510, 512 and 514 are determined at two second intervals. If VT detection criteria requires at least 8 out of 12 consecutive RR intervals are less than a VT detection interval of 300 ms or less, one or two activity counts 510 and 512 may occur during the eight to twelve RR intervals during the series of fast VS events 522 leading up to VT detection 524. In other cases, when a greater number of RR intervals are required to make a VT detection, e.g., if at least 16 out of 24 RR intervals are required to fall in a VT interval zone, three or more activity counts may occur during the series of VS events 522 that lead to VT detection criteria being satisfied. All of the activity counts determined after onset of a fast rate, i.e., the onset 525 of VS events 522 that satisfy VT detection criteria, may be compared to the unstable rhythm threshold 506. A predetermined percentage of activity counts determined after the onset 525 of the fast rate may be required to be less than the unstable rhythm threshold.

Figure 8:
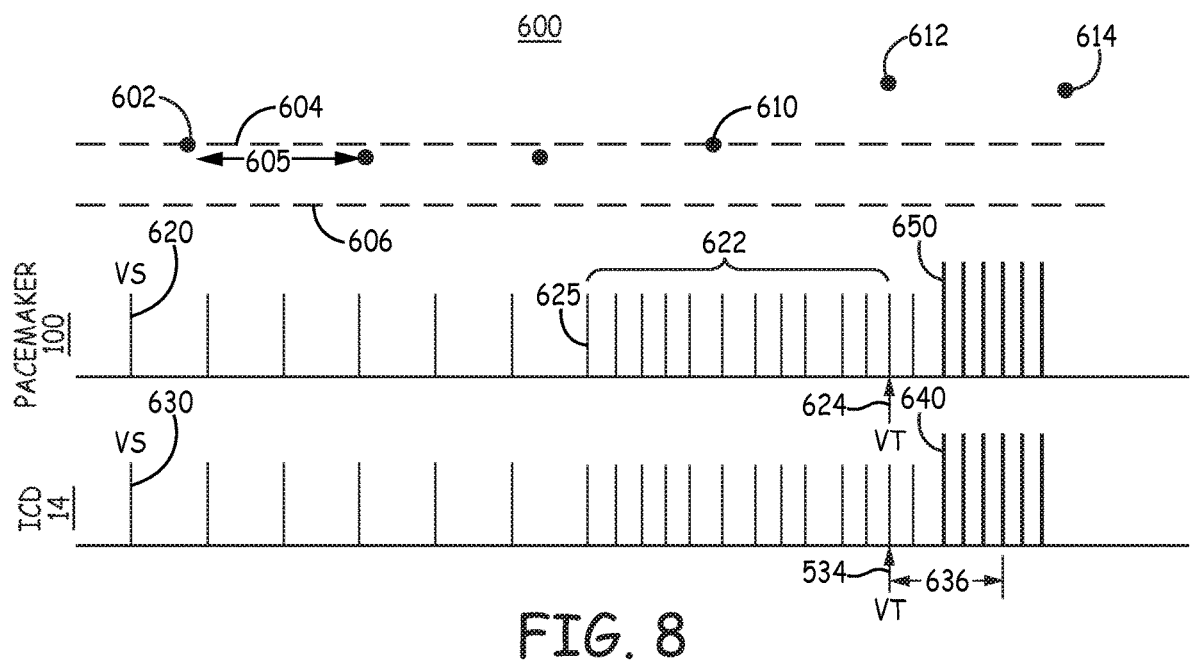
FIG. 8 is a timing diagram illustrating the operations of the IMD system of FIG. 1 according to another example.

In the examples of FIG. 7 and FIG. 8 below, the activity counts are determined at regular sampling intervals 505 before and during VT detection. In other examples, activity metrics may be determined more often, i.e., at shorter sampling intervals, to obtain more activity metrics for confirming a hemodynamically unstable rhythm. The activity metrics determined more frequently may be compared to criteria appropriately adjusted for change in sampling rate. For example, if activity counts are determined over 2-second intervals when a fast rate is not being detected, activity counts may be determined every one second when a fast rate is being detected. The unstable rhythm threshold 506 may be set taking into account the shorter activity count interval.

In one example, if at least one of the two most recent activity counts 510 and 512 is less than the unstable rhythm detection threshold 506, the VT detection 524 is confirmed as a hemodynamically unstable rhythm. In another example, if both of the two most recent activity counts 510 and 512 are equal to or less than the LR set point 504 and at least one is less than the unstable rhythm detection threshold 506, a hemodynamically unstable rhythm is confirmed.

In another example, at least two consecutive activity counts are required to be less than the unstable rhythm detection threshold 506 in order to confirm the VT detection 524 as a hemodynamically unstable rhythm. The two consecutive activity counts may both be before VT detection 524, e.g., activity counts 510 and 512 during VS events 522, or one may be before VT detection 524 and one after, e.g., activity counts 512 and 514. In some examples, pacemaker control module 206 may identify the activity counts 512 and 514 occurring closest in time to the VT detection 524 and if both activity counts 512 and 514 are less than the unstable rhythm detection threshold 506, the VT detection 524 is confirmed as a hemodynamically unstable rhythm. In response to confirming a hemodynamically unstable rhythm, pacemaker 100 withholds ATP therapy delivery.

In some cases, the pacemaker control module 206 may not be limited to using complete sampling intervals 505 for obtaining activity counts for confirming a hemodynamically unstable rhythm. For example, an activity count 512, obtained after the onset 525 of the fast rate and accumulated over a complete sampling interval 505, may be summed with a partial activity count 513 that has been reached upon VT detection 524 during an activity count sampling interval 505. The sum of the complete activity count 512 and the partial activity count 513 may be compared to a scaled unstable rhythm detection threshold that has been adjusted from the established unstable rhythm detection threshold 506 to take into account the total time interval over which the summed activity counts 512 and 513 were accumulated. To illustrate, if one complete activity count at a sampling interval of 2 seconds and one partial activity count accumulated over 1 second are summed, the total time interval is 1.5 activity count sampling intervals. The complete and partial activity counts may be summed to obtain a 3 second count that is compared to 1.5 times the unstable rhythm detection threshold 506.

In another example, an activity count counter may be started upon detecting one or more fast RR intervals such that an activity count is started near the onset 525 of the VS events 522 that lead to VT detection 524. The activity count counter is allowed to run until VT detection 524 occurs (or until a VT interval counter is reset due to VT detection criteria not being met at which time it may also be reset). The activity count reached upon VT detection 524 is compared to a scaled threshold that has been adjusted from the unstable rhythm detection threshold 506 based on a ratio of the total time that the activity count was accumulated during VT detection to the activity count sampling interval 505 that was used to establish threshold 506. For example, if an activity count is accumulated over 2.5 seconds during VT detection, the activity count may be compared to 1.25 times the unstable rhythm detection threshold 506 established based on 2-second activity counts. If the accumulated activity count is less than 1.25 times the unstable rhythm detection threshold 506, a hemodynamically unstable rhythm is confirmed. In this way, an activity metric may be determined during a fast rate for confirming an unstable rhythm that is not limited to an activity metric sampling interval that is used for determining the activity metric when a fast rate or VT is not being detected.

ICD 14 senses ventricular events 530 from a received ECG signal and depending on the particular detection algorithms implemented in pacemaker 100 and ICD 14, ICD 14 is expected to make a VT detection 534 at approximately the same time as the VT detection 524 made by pacemaker 100. In response to VT detection 534, ICD 14 determines if any ATP pulses are sensed during a delay interval 536. Delay interval 536 may be all or a portion of a capacitor charging time during which high voltage capacitors are charged in preparing for delivering a shock pulse if one is needed. Accordingly in some examples, ICD capacitor charging and ICD monitoring for ATP pulses being delivered by pacemaker 100 may occur simultaneously after VT detection 534. In other examples, capacitor charging may not begin until after an initial check for ATP pulses is made. Capacitor charging may begin at the beginning, during or expiration of a delay interval 536. The delay time 536 may be a predetermined time interval during which ICD 14 monitors for ATP pulses or may not be predefined and instead be the capacitor charge time. If ATP pulses are detected at any time during the capacitor charge time, the shock pulse 540 is delayed.

In the example shown, capacitor charging is complete upon expiration of delay time 536, which may be the required time to charge high voltage capacitors of therapy delivery module 84 to deliver a programmed shock energy. Since no ATP pulses are detected during delay time 536 (because pacemaker 100 has confirmed a hemodynamically unstable rhythm based on the activity counts 512 and/or 514 and has withheld ATP), ICD 14 delivers a shock 540 to terminate the unstable rhythm. In some cases, pacemaker 100 will deliver post-shock pacing pulses 550 if ventricular events are not sensed due to post-shock asystole or bradycardia. In this way, shock 540 may be delivered promptly upon completing capacitor charging after the VT detection 534 and confirmation that pacemaker 100 has confirmed a hemodynamically unstable rhythm based on the absence of ATP during the delay interval (or capacitor charging time) 536.

FIG. 8 is a timing diagram 600 illustrating the operations of ICD 14 and pacemaker 100 according to another example. Pacemaker control module 206 determines activity counts 602, 610, 612 and 614 (or another activity metric) at regular activity count sampling intervals 605. The LR set point 604 and the unstable rhythm detection threshold 606 are shown by dashed lines.

Pacemaker 100 senses ventricular events 620. VT detection 624 is made in response to a series of ventricular sensed events 622 meeting VT detection criteria, e.g., based on RR intervals. Upon the VT detection 624, pacemaker 100 analyzes one or more activity counts, e.g., 610, 612 and/or 614, occurring immediately prior to and/or immediately following VT detection 624. In one example, if at least the most recent activity count 612 preceding VT detection 624 is greater than the unstable rhythm detection threshold 606, the VT is detected as a hemodynamically stable rhythm. The pacemaker control module 206 controls pulse generator 202 to deliver ATP pulses 650 to terminate the VT.

In another example, if the most recent two activity counts 610 and 612 are both greater than the unstable rhythm detection threshold 606 or at least one of the most recent two activity counts 610 and 612 is greater than the LR set point 604, the VT is determined to be hemodynamically stable, i.e., potentially treatable with ATP. One or more consecutive activity counts 610, 612 immediately preceding the VT detection 624 (after onset 625 of the fast rate) and/or one or more activity counts 614 immediately after the VT detection 624 may be used in confirming a hemodynamically unstable rhythm. As described above, all of the activity counts that occur during a series of RR intervals 622 that meet VT detection criteria, partial activity counts accumulated during VT detection, and/or one or more activity counts immediately following VT detection 624 may be used to confirm a hemodynamically unstable rhythm.

ICD 14 senses ventricular events 630 and is expected to make a VT detection 634 at approximately the same time as the VT detection 624 made by pacemaker 100. In response to VT detection 634, ICD 14 determines if any ATP pulses are sensed during a delay interval 636. Delay interval 636 may be all or a portion of a capacitor charging time during which high voltage capacitors are charged in preparing for delivering a shock pulse if one is needed. In this example, ATP pulses 650 are sensed by ICD 14. ATP is detected by ICD 14 based on the rate of the pacing pulse sensed events 640. For example, ICD 14 may detect ATP based on a rate of pacing pulse sensed events 640 at an expected ATP pulse rate or at a rate faster than the series of VS events 622 that led to VT detection 634.

In response to detection ATP, ICD processor and control module 80 withholds a shock therapy. If capacitor charging has already begun over interval 636, the ICD processor and control module 80 may wait until ATP pulses 650 are no longer detected and determine if the VT is still being detected. The shock therapy may be delivered after ATP if VT is still being detected. If the VT is successfully terminated by ATP pulses 650, the HV capacitors can be discharged through a non-therapeutic load and the scheduled shock pulse is cancelled.

Figure 9:
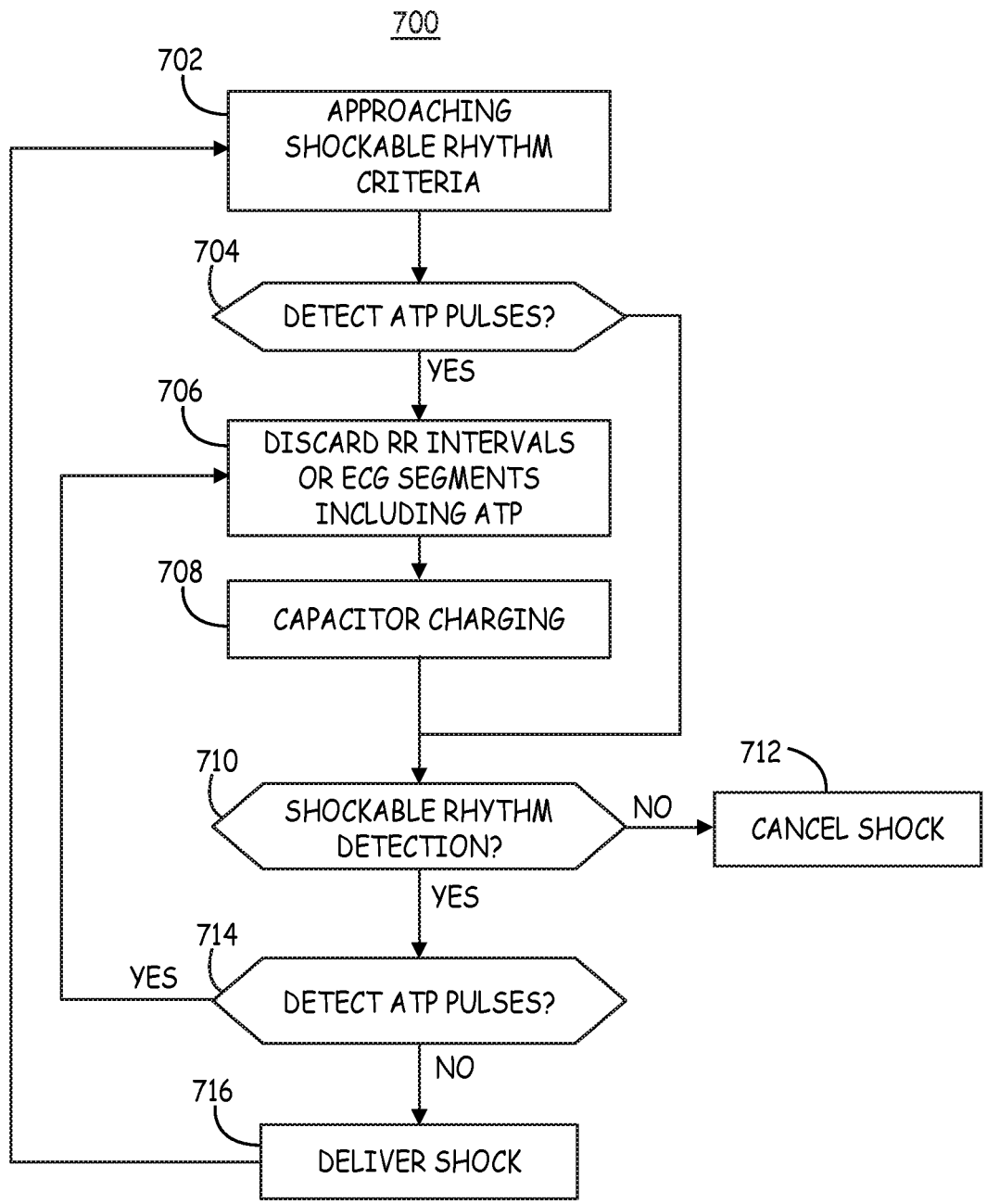
FIG. 9 is a flow chart of a method for controlling shock delivery by the ICD of FIG. 1 in the presence of the intracardiac pacemaker.

FIG. 9 is a flow chart 700 of a method for controlling shock delivery by ICD 14 in the presence of intracardiac pacemaker 100. At block 702, ICD 14 is approaching detection of a shockable, VT rhythm based on VT detection criteria. For example, the ICD 14 may detect a threshold number of fast RR intervals in a VT interval zone but a required number of VT intervals for detecting a shockable rhythm may not yet be reached. In another example, an n-second ECG signal may be classified as a shockable segment based on signal morphology and/or RR interval analysis, but a required number of shockable segments for detecting a shockable rhythm has not yet been detected.

If shockable rhythm detection criteria have been partially satisfied, the ICD 14 may begin monitoring for ATP pulses. ICD processor and control module 80 determines if ATP is detected at block 406 based on pacing pulse sensed event signals received from sensing module 86 meeting ATP detection criteria. If ATP is detected, the RR intervals prior to ATP detection may be discarded for purposes of detecting a shockable rhythm by ICD 14 at block 706. In some examples, shockable rhythm criteria may include counting a threshold number of VT intervals. In this case, the VT interval counters may be cleared in response to detecting ATP or any detected RR intervals that include ATP pulse detection are discarded for the purposes of detecting a shockable rhythm.

In another example, if a 3-second segment is detected as a shockable segment based on morphology analysis, the cardiac signal analyzer 90 is approaching shockable rhythm detection. At least two out three n-second segments may be required to be classified as shockable segments in order to detect a shockable rhythm. If ATP is detected during any of the three n-second segments, that segment may be discarded for the purposes of detecting a shockable rhythm. In this way, shockable rhythm detection, and therefore a subsequent shock, may be delayed by the detection of ATP being delivered by the pacemaker 100.

In some cases, ECG-based shockable rhythm detection criteria must be fully satisfied after the detected ATP without using any RR intervals or ECG signal segments that occurred prior to the detected ATP. In other examples, if shockable rhythm detection criteria was partially satisfied prior to detecting ATP, a reduced number of VT intervals, shockable ECG segments, or other shockable rhythm detection criteria may be applied after the ATP detection to allow more rapid shockable rhythm detection after ATP to lead to prompt shock delivery in case the ATP does not terminate the tachyarrhythmia.

At block 708, capacitor charging may be started in response to detecting ATP in anticipation that a shock may be needed, even before ICD 14 has reached a shockable VT rhythm detection. In other examples, capacitor charging is not started until the ICD detects a shockable rhythm (i.e., after decision block 710). If shockable rhythm criteria are satisfied after detecting ATP, as determined at decision block 710, the ICD 14 may verify ATP is not being detected at block 714 prior to shock delivery at block 716.

If ATP is detected by ICD 14 after shockable rhythm detection criteria are satisfied but before shock delivery, e.g., before capacitor charging is completed, the ICD 14 may return to block 706 and discard RR intervals and/or ECG signal segments that led to the shockable rhythm detection. In other examples, redetection criteria are applied after detecting the ATP pulses. Shockable rhythm redetection criteria applied after an initial shockable rhythm detection and ATP detection may require fewer RR intervals and/or ECG time segments meeting redetection criteria than the number of RR intervals and/or ECG time segments required to make the initial shockable rhythm detection.

If ATP is not detected at block 714, a shock is delivered at block 716 by ICD 14 according to programmed shock therapy control parameters. If a shockable rhythm is not detected after ATP detection, as determined at block 710, a scheduled or expected shock is canceled at block 712. Partially or fully charged high voltage capacitors may be allowed to discharge through a non-therapeutic load.

Thus, various embodiments of a medical device system and method have been described for controlling cardiac electrical stimulation therapies in an IMD system including an intracardiac pacemaker and an ICD. However, one of ordinary skill in the art will appreciate that various modifications may be made to the described embodiments without departing from the scope of the following claims.

The invention claimed is:

1. A system comprising:
 a first device comprising:
  an electrical sensing module configured to obtain a sensed cardiac electrical signal; and
  a cardiac signal analyzer configured to:
   detect partial satisfaction of a tachyarrhythmia detection criteria within the sensed cardiac electrical signal;
   in response to detecting partial satisfaction of the tachyarrhythmia detection criteria, begin monitoring for anti-tachycardia pacing (ATP) applied by a second device separate from the first device;
   detect ATP applied by the second device; and
   adjust the tachyarrhythmia detection criteria in response to detecting ATP.

2. The system of claim 1,
 wherein the sensing module is further configured to detect cardiac events attendant to depolarization of a ventricle within the sensed cardiac electrical signal, and
 wherein the cardiac signal analyzer is further configured to:
  determine a plurality of R-R intervals between consecutively detected cardiac events; analyze at least one of the plurality of the determined R-R intervals; and
  detect partial satisfaction of a tachyarrhythmia detection criteria within a sensed cardiac electrical signal based at least on the analysis of the R-R intervals.

3. The system of claim 2, wherein the cardiac signal analyzer is configured to:
 maintain a counter that tracks a number of R-R intervals that are within a tachyarrhythmia interval zone; and
 detect partial satisfaction of a tachyarrhythmia detection criteria when the counter is greater than a first threshold number and less than a second threshold number for detecting a tachyarrhythmia.

4. The system of claim 3, wherein the cardiac signal analyzer is configured to adjust the tachyarrhythmia detection criteria by resetting the counter in response to detecting ATP.

5. The system of claim 2, wherein the cardiac signal analyzer is configured to adjust the tachyarrhythmia detection criteria by discarding R-R intervals occurring prior to detecting ATP from tachyarrhythmia detection analysis.

6. The system of claim 1, wherein the cardiac signal analyzer is configured to:
 analyze a morphology of a plurality of segments of the sensed cardiac electrical signal; classify ones of the plurality of segments as shockable based on the analysis of the morphology; and
 detect partial satisfaction of a tachyarrhythmia detection criteria when a number of the plurality of segments classified as shockable is greater than a first threshold number and less than a second threshold number for detecting a tachyarrhythmia.

7. The system of claim 6, wherein the cardiac signal analyzer is configured to adjust the tachyarrhythmia detection criteria by discarding the plurality of segments occurring prior to detecting ATP from tachyarrhythmia detection analysis.

8. The system of claim 1, wherein the cardiac signal analyzer is configured to adjust the tachyarrhythmia detection criteria by discarding from tachyarrhythmia detection analysis at least one of portions of the sensed cardiac electrical signal that occur prior to detecting ATP or portions of the sensed cardiac electrical signal that include the detected ATP.

9. The system of claim 8, the adjusted tachyarrhythmia detection criteria applied after detecting ATP allows more rapid tachyarrhythmia detection than the tachyarrhythmia detection criteria applied before detecting ATP.

10. The system of claim 1, wherein the cardiac signal analyzer is configured to detect a tachyarrhythmia in response to the adjusted tachyarrhythmia detection criteria being met, the first device further comprising a therapy delivery module configured to deliver a shock in response to detecting the tachyarrhythmia.

11. The system of claim 1, wherein the cardiac signal analyzer is configured to detect partial satisfaction of a ventricular tachycardia (VT) detection criteria.

12. A method comprising:
 detecting, by a first device, partial satisfaction of a tachyarrhythmia detection criteria within a sensed cardiac electrical signal;
 in response to detecting partial satisfaction of the tachyarrhythmia detection criteria, begin monitoring, by the first device, for anti-tachycardia pacing (ATP) applied by a second device separate from the first device;
 detecting, by the first device, ATP applied by the second device; and
 adjusting, by the first device, the tachyarrhythmia detection criteria in response to detecting ATP.

13. The method of claim 12, further comprising:
 obtaining the sensed cardiac electrical signal;
 detecting cardiac events attendant to depolarization of a ventricle within the sensed cardiac electrical signal;
 determining a plurality of R-R intervals between consecutively detected cardiac events; and
 maintaining a counter that tracks a number of plurality of R-R intervals that are within a tachyarrhythmia interval zone,
 wherein detecting partial satisfaction of the tachyarrhythmia detection criteria comprises detecting partial satisfaction of the tachyarrhythmia detection criteria when the counter is greater than a first threshold number and less than a second threshold number for detecting a tachyarrhythmia.

14. The method of claim 13, wherein adjusting the tachyarrhythmia detection criteria comprises at least one of resetting the counter in response to detecting ATP or discarding R-R intervals occurring prior to detecting ATP from tachyarrhythmia detection analysis.

15. The method of claim 12, further comprising:
 analyzing a morphology of a plurality of segments of the sensed cardiac electrical signal; and
 classifying ones of the plurality of segments as shockable based on the analysis of the morphology,
 wherein detecting partial satisfaction of a tachyarrhythmia detection criteria comprises detecting partial satisfaction of a tachyarrhythmia detection criteria when a number of the plurality of segments classified as shockable is greater than a first threshold number and less than a second threshold number for detecting a tachyarrhythmia.

16. The method of claim 15, wherein adjusting the tachyarrhythmia detection criteria comprises discarding the plurality of segments occurring prior to detecting ATP from tachyarrhythmia detection analysis.

17. The method of claim 12, wherein adjusting the tachyarrhythmia detection criteria comprises discarding from tachyarrhythmia detection analysis at least one of portions of the sensed cardiac electrical signal that occur prior to detecting ATP or portions of the sensed cardiac electrical signal that include the detected ATP.

18. The method of claim 17, wherein the adjusted tachyarrhythmia detection criteria applied after detecting ATP allows more rapid tachyarrhythmia detection than the tachyarrhythmia detection criteria applied before detecting ATP.

19. The method of claim 12, further comprising:
 detecting a tachyarrhythmia in response to the adjusted tachyarrhythmia detection criteria being met; and
 delivering a shock in response to detecting the tachyarrhythmia.

20. The method of claim 12, wherein detecting partial satisfaction of a tachyarrhythmia detection criteria comprises detecting partial satisfaction of a ventricular tachycardia (VT) detection criteria.

* * * * *